(12) United States Patent
Van Der Schaaf et al.

(10) Patent No.: US 6,872,853 B1
(45) Date of Patent: Mar. 29, 2005

(54) POLYMORPHIC FORMS OF SERTRALINE HYDROCHLORIDE

(75) Inventors: Paul Adriaan Van Der Schaaf, Allschwil (CH); Franz Schwarzenbach, Frenkendorf (CH); Hans-Jörg Kirner, Pratteln (CH); Martin Szelagiewicz, Münchenstein (CH); Claudia Marcolli, Zürich (CH); Andreas Burkhard, Basel (CH); Regine Peter, Birsfelden (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 110 days.

(21) Appl. No.: 10/111,947

(22) PCT Filed: Oct. 23, 2000

(86) PCT No.: PCT/EP00/10416

§ 371 (c)(1),
(2), (4) Date: Apr. 26, 2002

(87) PCT Pub. No.: WO01/32601

PCT Pub. Date: May 10, 2001

(30) Foreign Application Priority Data

Oct. 29, 1999 (EP) .............................................. 99810981

(51) Int. Cl.$^7$ .......................................... C07C 211/42
(52) U.S. Cl. ....................................................... 564/308
(58) Field of Search ........................................ 564/308

(56) References Cited

U.S. PATENT DOCUMENTS

| | | | |
|---|---|---|---|
| 4,536,518 A | 8/1985 | Welch, Jr. et al. .......... | 514/647 |
| 5,082,970 A | 1/1992 | Braish ........................ | 564/424 |
| 5,248,699 A | 9/1993 | Sysko et al. ................ | 514/647 |
| 5,463,126 A | 10/1995 | Williams .................... | 564/222 |
| 5,734,083 A | 3/1998 | Wilson et al. .............. | 564/308 |
| 6,452,054 B2 | 9/2002 | Aronhime et al. | |
| 6,495,721 B1 | 12/2002 | Schwartz et al. ........... | 564/308 |
| 6,500,987 B1 | 12/2002 | Schwartz et al. | |
| 6,600,073 B1 | 7/2003 | Schwartz et al. | |

FOREIGN PATENT DOCUMENTS

| | | |
|---|---|---|
| EP | 0928784 | 7/1999 |
| JP | 2000-26378 | 1/2000 |
| WO | 98/27050 | 6/1998 |
| WO | 00/32551 | 6/2000 |

OTHER PUBLICATIONS

U.S. patent application Ser. No. 10/198,546, Schwartz et al., filed Jul. 18, 2003.

U.S. patent application Ser. No. 10/243,293, Aronhime et al., filed Sep. 13, 2002.

U.S. patent application Ser. No. 10/218,863, Schwartz et al., filed Aug. 13, 2002.

*Primary Examiner*—Samuel Barts
(74) *Attorney, Agent, or Firm*—Kevin T. Mansfield

(57) ABSTRACT

A cystalline form of sertraline hydrochloride was found, referred to hereinafter as polymorphic form CSC2 having a dissolution rate which surprisingly will increase rate of absorption of a drug. Furthermore, different crystalline forms of sertraline hydrochloride alcohol solvates, crystalline forms of sertraline hydrochloride hydrates, referred to hereinafter as polymorphic form CSC1, a process for the preparation of the amorphous form of sertraline hydrochloride, and different processes for the preparation of polymorphic forms I, II, V, and T1 are disclosed.

6 Claims, 28 Drawing Sheets

POLYMORPHIC FORMS OF SERTRALINE HYDROCHLORIDE

The present invention relates to crystalline polymorphic forms and the amorphous form of (1S-cis)-4-(3,4-dichlorophenyl)-1,2,3,4-tetrahydro-N-methyl-1-naphthalenamine hydrochloride, i.e. sertraline hydrochloride, to methods for preparing them, and methods for preparing known polymorphic forms of sertraline hydrochloride.

Sertraline hydrochloride is useful as an antidepressant and anorectic agent, and is also useful in the treatment of chemical dependencies, anxiety-related disorders and premature ejaculation, and is described in U.S. Pat. No. 4,536,518 (Pfizer Inc.).

Sertraline hydrochloride can exist in different crystalline forms, polymorphic forms, which differ from each other in their stability, physical properties, spectral data and methods of preparation.

Sertraline has the following structural chemical formula:

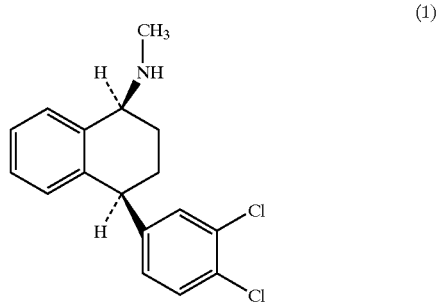

(1)

U.S. Pat. No. 4,536,518 (Pfizer Inc.) discloses the synthesis of sertraline hydrochloride. The amine is dissolved in a mixture of diethyl ether and ethyl acetate and reacted with hydrogen chloride gas. The reference states that the compounds of this invention may exist in different polymorphic forms, i.e. different crystalline forms. The reference does not refer to specific polymorphic crystalline forms of sertraline hydrochloride.

U.S. Pat. No. 5,248,699 (Pfizer Inc.) discloses 5 polymorphic forms of sertraline hydrochloride (I, II, III, IV, and V) as well as methods for preparing them. The reference further discloses that the synthetic procedure described and exemplified in U.S. Pat. No. 4,536,518 produces the sertraline hydrochloride polymorph designated herein as Form II.

U.S. Pat. No. 5,734,083 (Torcan Chemical Ltd.) discloses a further polymorphic form of sertraline hydrochloride (=T1), together with the process of preparation.

Although it is disclosed in U.S. Pat. No. 5,248,699 (Pfizer Inc.) that polymorphic form I exhibits the greatest stability of the crystalline forms of sertraline hydrochloride, the solubility of this form may be insufficient for successful application. For example, the rate of absorption of a drug is dependent upon the dissolution rate. The dissolution rate and the rate of absorption will either increase or decrease depending upon the polymorph present. The most stable polymorph will have the lowest solubility and in many cases the slowest dissolution rate. Other less stable polymorphs will usually have higher dissolution rates. [Stephen R. Byrn in "Solid-State Chemistry of Drugs", Academic Press, New York, 1982].

A crystalline form of sertraline hydrochloride was found, referred to hereinafter as polymorphic form CSC2 having a high solubility in combination with a good thermal stability.

Furthermore, the present invention refers to different crystalline forms of sertraline hydrochloride alcohol solvates, crystalline forms of sertraline hydrochloride hydrates, referred to hereinafter as polymorphic form CSC1, a process for the preparation of the amorphous form of sertraline hydrochloride, and different processes for the preparation of polymorphic forms I, II, V, and T1.

General Definitions

Sertraline Hydrochloride Alcohol Solvates

Substances formed by combination of the compound sertraline hydrochloride with an alcohol of the general formula R—OH, wherein A is an organic group. These substances have the general formula $(C_{17}H_{17}Cl_2N.HCl)(ROH)_X$ wherein X is between 0.5 and 2.

Sertraline Hydrochloride Hydrates

Substances formed by combination of the compound sertraline hydrochloride with water. These substances have the general formula $(C_{17}H_{17}Cl_2N.HCl)(H_2O)_X$ wherein X is between 0 and 4 (in which X=0 stands for the desolvated hydrate).

The crystalline polymorph CSC2 exhibits a characteristic X-ray powder diffraction pattern with characteristic peaks at diffraction angles 2 θ in degrees of 12.2, 15.7, 17.2, 18.3, 22.8, 23.0, 24.4 and 30.7 as depicted in FIG. 19. Here and in the following the spectra are measured with a diffractometer using copper radiation.

A discussion of the theory of X-ray powder diffraction patterns can be found in "X-ray diffraction procedures" by H. P. Klug and L. E. Alexander, J. Wiley, New York (1974).

The crystalline polymorph CSC2 upon heating is transformed into form V at temperatures of about >120° C., whereupon a second transformation takes place into form III at temperatures of about >160° C. (experiment performed in a DSC apparatus with heating rate of 20° C./minute).

The crystalline polymorph CSC2 is further characterized by the Raman absorption spectrum having the following characteristic absorption bands, expressed in wave number $(cm^{-1})$: 3052 (s), 2976 (s), 2963 (s), 2943 (s), 2885 (m), 2862 (m), 1590 (s), 1049 (m), 744 (m), 676 (s), 490 (m), 477 (m), 364 (m), 349 (m), 237 (m), 203 (m), 181 (s); [(m)=medium intensity; (s)=strong intensity] as depicted in FIG. 20.

The present invention also relates to crystalline forms of sertraline hydrochloride hydrates, referred to hereinafter as form CSC1. The crystalline form of sertraline hydrochloride hydrate changes with the amount of water present in the crystal as hydrate. With an X-ray diffractometer in which the humidity (RH) of the atmosphere can be controlled during the measurements at least 5 distinct different X-ray powder diffraction patterns with characteristic peaks expressed in 2θ can be distinguished (FIG. 13):

CSC1 90% RH (wet): 4.0; 12.0; 19.7; 20.0; 22.7; 24.0; 26.6; 30.7; 34.7

CSC1 90% RH: 4.0; 4.2; 16.2; 17.2; 19.9; 20.7; 21.2; 22.7; 24.1; 25.2; 27.3; 29.9; 30.7; 31.3; 31.8

CSC1 50% RH: 4.7; 9.3; 13.9; 15.1; 16.0; 16.4; 16.8; 17.5; 17.9; 19.3; 20.5; 21.1; 21.5; 22.2; 23.0; 23.7; 24.1; 24.8; 25.8; 31.2; 32.2; 33.5

CSC1 20% RH: 4.9; 9.7; 12.1; 14.1; 15.4; 16.5; 17.0; 18.1: 19.4; 21.9: 22.3; 24.8; 25.9; 31.7

CSC1 0% RH: 5.0; 14.0; 15.6: 16.5; 18.1; 19.5; 22.1: 22.9; 25.1; 25.9; 30.3; 33.5.

The present invention also refers to different crystalline forms of sertraline hydrochloride alcohol solvates, for example sertraline hydrochloride ethanol solvate, sertraline hydrochloride isopropanol solvate and sertraline hydrochloride methanol solvate.

The crystalline form of sertraline hydrochloride ethanol solvate exhibits a characteristic X-ray powder diffraction pattern with characteristic peaks expressed in 2 θ at 12.7, 15.1, 15.8, 16.0, 17.0, 17.7, 17.9, 20.1. 20.5, 20.7, 21.0, 21.3, 21.9, 22.8, 23.1, 23.9, 24.4, 25.0, 25.4, 26.0, 26.4, 27.0, 28.6, 29.1, 31.3, 31.7, 32.0 and 32.9 as depicted in FIG. 22.

The crystalline form of sertraline hydrochloride ethanol solvate is further characterized by the Raman absorption spectrum having the following characteristic absorption bands, expressed in wave number ($cm^{-1}$): 3060 (s), 2974 (s), 2945 (s), 2878 (s), 1590 (s), 1046 (s), 740 (s), 672 (s), 504 (m), 475 (m), 462 (m), 377 (m), 361 (m), 232 (s), 211 (s), 197 (s), 182 (s), 144 (s), 104 (s) [(m)=medium intensity; (s)=strong intensity] as depicted in FIG. 23.

The crystalline form of sertraline hydrochloride isopropanol solvate exhibits a characteristic X-ray powder diffraction pattern with characteristic peaks expressed in 2 θ at 6.4, 10.7, 12.9, 14.2, 15.0, 15.2. 16.3, 17.9, 19.1, 19.9, 20.4, 22.4, 22.9, 23.9, 24.5, 25.3, 25.5, 25.9, 27.8, 28.8, 29.6, 30.2, 33.0 and 34.2 as depicted in FIG. 24.

The crystalline form of sertraline hydrochloride isopropanol solvate is further characterized by the Raman absorption spectrum having the following characteristic absorption bands, expressed in wave number ($cm^{-1}$): 3057 (s), 2975 (s), 2939 (s), 2883 (m), 2865 (m), 1591 (s), 1043 (s), 744 (m), 676 (s), 505 (m), 491 (m), 477 (m), 461 (m), 355 (m), 229 (m), 196 (s), 182 (s), 148 (s), 125 (s) [(m)=medium intensity; (s)=strong intensity] as depicted in FIG. 25.

The crystalline form of sertraline hydrochloride methanol solvate exhibits a characteristic X-ray powder diffraction pattern with characteristic peaks expressed in 2 θ at 7.4, 9.7, 12.0, 12.4, 12.8, 14.3, 16.0. 16.2, 17.9, 20.3, 20.7, 21.0, 22.1, 23.1, 23.6, 24.2, 24.4, 24.9, 25.7. 26.6, 27.1, 29.5, 30.6, 31.4, 31.9, 32.5, 33.2, 34.1, 35.1, 36.5, 38.0 as depicted in FIG. 28.

The crystalline form of sertraline hydrochloride methanol solvate is further characterized by the Raman absorption spectrum having the following characteristic absorption bands, expressed in wave number ($cm^1$): 3061 (s), 2975 (s), 2959 (s), 2941 (s), 2876 (s), 1591 (s), 1046 (s), 740 (s), 673 (s), 505 (m), 477 (m), 462 (m), 378 (m), 361 (m), 234 (m), 213 (s), 197 (s), 179 (s), 129 (s), [(m)=medium intensity; (s)=strong intensity] as depicted in FIG. 21.

The present invention also refers to the amorphous form sertraline hydrochloride. This amorphous form of sertraline hydrochloride gives an X-ray powder diffraction pattern with a broad bump with a maximum in 2 θ between 25 and 30, and some broad peaks at 16 and 23 as depicted in FIG. 26.

The amorphous form of sertraline hydrochloride is further characterized by the Raman absorption spectrum having the following characteristic absorption bands, expressed in wave number ($cm^{-1}$): 3054 (s), 2970 (s), 2933 (s), 2872 (s), 1590 (s), 1043 (s), 745 (m), 676 (s), 491 (m), 478 (m), 359 (m), 236 (m), 206 (s), 181 (s), 130 (s), [(m)=medium intensity; (s)=strong intensity], as depicted in FIG. 27.

The sertraline hydrochloride polymorphic form CSC2 may be formed by the addition of a solution of sertraline free amine in a solvent, preferably ethanol to a solution of hydrogen chloride in water, or by addition of an excess of a solution of hydrogen chloride in water to a solution of sertraline free amine. Preferably, the reaction is performed at temperatures from about 5 to 35° C., most preferably at room temperature.

The process for the preparation of sertraline hydrochloride polymorphic form CSC2 is a further object of the present invention.

The hydrochloride alcohol solvates may be formed by crystallizaton or recrystallization of sertraline hydrochloride from the corresponding alcohol, preferably selected from ethanol, isopropanol and methanol or by prolonged stirring of a suspension of sertraline hydrochloride in the corresponding alcohol at temperatures from about −20 to 40° C., most preferably at room temperature.

The process for the preparation of the hydrochloride alcohol solvates is a further object of the present invention.

The sertraline hydrochloride polymorphic form CSC1 may be formed when the reaction of sertraline free amine with hydrogen chloride is carried out in the presence of water at temperatures of about 5 to 40° C., most preferably at room temperature, or by the crystallization or recrystallization of sertraline hydrochloride from water at temperatures between about 5 and 40° C.

The sertraline hydrochloride polymorph form CSC1 may also be formed by recrystallization of any polymorphic form of sertraline hydrochloride from water.

The sertraline hydrochloride polymorph form CSC1 may also be formed upon stirring a suspension of any polymorphic form of sertraline hydrochloride, except for polymorphic form I, in aqueous solutions of hydrogen chloride at a pH between 0 and 2, most preferably at pH about 1, at temperatures between 5 and 40° C.

The process for the preparation of the sertraline hydrochloride polymorphic form CSC1 is a further object of the present invention.

A still further object of the present invention is a process for the preparation of amorphous sertraline hydrochloride. Amorphous sertraline hydrochloride may be formed after addition of hydrogen chloride gas to sertraline free amine in a solvent like diethyl ether at temperatures between about 0 and 30°, most preferably at temperatures between 0 and 10° C.

A still further object of the present invention is a process for the preparation of polymorphic form T1. Sertraline hydrochloride polymorphic form T1 may be formed when the reaction of sertraline free amine with hydrogen chloride is carried out in a mixture of diethyl ether and ethyl acetate, or in dibutyl ether at temperatures between about 0 and 30° C.

A still further object of the present invention is a process for the preparation of polymorphic form I.

Sertraline hydrochloride polymorphic form I may be formed from a non-alcoholic suspension of amorphous sertraline hydrochloride, or polymorphic form CSC1, or polymorphic form CSC2, or a sertraline hydrochloride alcohol solvate upon prolonged agitation, or with faster reaction times after seeding with some crystals of sertraline hydrochloride polymorphic form I.

A still further object of the present invention is a process for the preparation of polymorphic form II.

Sertraline hydrochloride polymorphic form II may be formed from a solution of sertraline free amine with some seeding crystals of form II before the addition of a solution of hydrogen chloride; or from a stirred suspension of sertraline hydrochloride polymorphic form V with some seeding crystals of sertraline hydrochloride polymorphic form II; or by drying a sertraline hydrochloride alcohol solvate at temperatures from about 0 to 30° C. in high vacuum (<1 mbar); or from stirred suspensions of sertraline hydrochloride polymorphic form CSC1, CSC2 or T1 with some seeding crystals of sertraline hydrochloride polymorphic form II.

Furthermore, Sertraline hydrochloride polymorphic form II may be formed according to a process, wherein a solution of sertraline free amine is seeded with some crystals of polymorphic form II and a solution of hydrogen chloride is added.

Preferably a solution of sertraline free amine in a ketone is used. Preferred are ketones of formula $R_1$—CO—$R_2$, wherein $R_1$ and $R_2$ are $C_1$–$C_4$alkyl. Examples for $R_1$ and $R_2$ are methyl, ethyl, n- or i-propyl and n-, s-, i- or t-butyl. $R_1$ is preferably methyl. $R_2$ is preferably methyl, ethyl or i-butyl. Examples of ketones are acetone, methyl ethyl ketone or methyl isobutyl ketone.

The solution of hydrogen chloride used can be, for example, a solution in an organic solvent, like a ketone as given above, or preferably an aqueous solution.

It is preferred to add the seeding crystals of polymorphic form II before addition of the solution of hydrogen chloride. Typical amounts of seeding crystals are 0.1 to 10 mol-%, based on the molar amount of sertraline.

A still further object of the present invention is a process for the preparation of polymorphic form V.

Sertraline hydrochloride polymorphic form V may be formed by drying a sertraline hydrochloride alcohol solvate at temperatures of about 50° to about 100° C. in medium vacuum (>10 mbar) or by healing sertraline hydrochloride polymorphic form CSC2 at temperatures from about 80° to about 150° C.

This invention also relates to a pharmaceutical composition comprising an amount of a polymorphic form CSC2, CSC1, the amorphous form or alcohol solvates of sertraline hydrochloride with any of the above characteristics effective in treating depressions, anxiety-related disorders, obesity, chemical dependencies, or addictions or premature ejaculations in a human, and a pharmaceutically acceptable carrier.

The polymorphic forms, hydrates, the amorphous form and alcohol solvates may be used as single components or mixtures.

The following examples will illustrate, but do not limit the scope of the present invention.

EXAMPLE 1

Preparation of Polymorph Form CSC2

A solution of 21 g sertraline free amine in 75 g ethanol is added dropwise over a period of 30 min to a stirred, aqueous solution of HCl (8 g 37% HCl/$H_2O$ in 200 ml water). At the end of the reaction the reaction mixture has a pH=3. Stirring is stopped and the crystals are allowed to separate from the solution overnight. The crystals are filtered of and washed with water (3×50 ml) and dried in vacuum (100 mbar) at 25° C. for 24 h.

The product, a white crystalline solid, is obtained in 92% yield (see FIGS. 19 and 20).

EXAMPLE 2

Preparation of the Sertraline Hydrochloride Ethanol Solvate 0.5 g sertraline hydrochloride is dissolved in 5 ml ethanol of 85° C. The resulting clear solution is placed in an ice/water bath and a white crystalline product is formed. These crystals are filtered and washed with a small amount of cold ethanol. The resulting product is dried at ambient temperature in air.

Sertraline hydrochloride ethanol solvate is obtained in 92% isolated yield (see FIGS. 22 and 23).

The formation of this ethanol solvate is independent from the polymorphic form of the starting material.

EXAMPLE 3

Preparation of the Sertraline Hydrochloride Isopropanol Solvate 0.5 g sertraline hydrochloride is dissolved in 10 ml isopropanol of 90° C. The resulting clear solution is cooled to 0° C. with stirring and a white crystalline product is formed. These crystals are filtered and washed with some cold isopropanol. The product is dried at ambient temperature in air.

Sertraline hydrochloride isopropanol solvate is obtained in 90% yield (see FIGS. 24 and 25).

The formation of this isopropanol solvate is independent from the polymorphic form of the starting material.

EXAMPLE 4

Preparation of the Sertraline Hydrochloride Methanol Solvate

A suspension of 0.4 g sertraline hydrochloride in 3 ml methanol is stirred for 30 min at room temperature. The white precipitate is filtered and dried in air at room temperature.

Sertraline hydrochloride methanol solvate is obtained in 89% yield (see FIGS. 21 and 28).

The formation of this methanol solvate is independent from the polymorphic form of the starting material.

EXAMPLE 5

Preparation of Polymorphic Form CSC1

0.5 ml of a 4 molar HCl solution in water is added dropwise to a suspension of 610 mg sertraline free amine in 7 ml water. The resulting white suspension is stirred at room temperature for 3 h and the pH changes from ca. 1 to ca. 6. The product is filtered and washed with water (2×3 ml) and subsequently dried in vacuum.

The product is obtained in 86% isolated yield. The X-ray and Raman spectra obtained depend on the dryness of the compound and also depend on the relative air humidity (RH) when recorded with conventional instruments (typical examples are depicted in FIGS. 9 to 12 and 14 to 18). When a wet sample is placed in a X-ray diffractometer in which the relative humidity of the atmosphere can be controlled the change in the X-ray spectra can be recorded (see FIG. 13).

EXAMPLE 6

Preparation of Amorphous Sertraline Hydrochloride

A solution of 2.85 g sertraline free amine (obtained after treating a solution of sertraline mandelate salt in ethyl acetate with a 2 molar solution of NaOH in water, followed by a standard organic work-up procedure) in 300 ml diethyl ether is cooled to 0° C. At this temperature, gaseous HCl is introduced in the reaction mixture for 30 minutes. The reaction mixture, a white suspension, is warmed to room temperature and stirred overnight under an argon atmosphere. The white suspension is filtered and the white product washed with diethyl ether (3×50 ml). The resulting white solid is dried at room temperature by blowing gently a stream of air over the product.

An X-ray powder diffraction pattern shows no significant signals indicating the amorphous form of the product.

Surprisingly, even a sample taken after 12 months shows only some broad signals at 2 θ=16 and 23° indicating the thermal stability of the amorphous form of sertraline hydrochloride (see FIGS. 26 and 27).

EXAMPLE 7

Preparation of Polymorphic Form T1

5.4 g of a HCl solution in acetone (prepared by mixing 9.47 g of an aqueous HCl solution (37 wt %) with 138 g acetone) is added dropwise to a solution of 1 g of sertraline free amine in 16 ml acetone. The white precipitate is filtered after stirring for 3 h and dried in vacuum (100 mbar) at ambient temperature.

The product is obtained in 82% yield.

Raman and X-ray powder diffraction studies show the product to be polymorphic form T1 (see FIGS. 7 and 8).

EXAMPLE 8

Preparation of Polymorph Form I from Sertraline Hydrochloride Isopropanolate

Heating sertraline hydrochloride isopropanol solvate at 70° C. in high vacuum (0.1 mbar) for 20 h results in the quantitative formation of sertraline hydrochloride polymorphic form I.

Raman and X-ray powder diffraction studies show the product to be polymorphic form I (see FIGS. 24 and 25).

EXAMPLE 9

Preparation of Polymorphic Form II 24 g sertraline free amine are dissolved in 280 ml acetone. To this solution 1.2 g sertraline hydrochloride polymorphic form II are added as seeding crystals. To this mixture are added dropwise 53.7 g of a solution of HCl in acetone (5.33 wt %) at room temperature. The resulting white suspension is stirred for an additional 2 h, filtered, and the resulting white product washed with acetone (2×20 ml). The product is dried in vacuum (0.1 mbar) for 16 h.

The product is obtained in 91% isolated yield.

Raman and X-ray powder diffraction studies show the product to be polymorphic form II (see FIGS. 3 and 4).

EXAMPLE 10

Preparation of Polymorphic Form II 50 g of sertraline free amine are dissolved in 500 ml acetone. This solution is clarified by filtration, and the clear solution is well stirred and heated to reflux temperature. At this temperature 2.5 g (5 mol %) of sertraline hydrochloride Form II are added after which directly the addition of the aqueous hydrogenchloride solution (32%) is started until pH<5. The resulting white suspension is cooled to −5° C. and sertraline hydrochloride is isolated by filtration and dried in vacuum. The sertraline is obtained as Form II.

EXAMPLE 11

Preparation of Polymorphic Form II 10 g sertraline free amine are dissolved in 85 ml methyl ethyl ketone. This solution is clarified by filtration, and the clear solution is well stirred and heated to 60° C. At this temperature 0.5 g (5 mol %) of sertraline hydrochloride Form II are added after which directly the addition of the aqueous hydrogenchloride solution (37%) is started until pH<5. The resulting white suspension is cooled to −5° C. and sertraline hydrochloride is isolated by filtration and dried in vacuum. The sertraline Is obtained as Form II.

EXAMPLE 12

Preparation of Polymorphic Form II 40 g sertraline are dissolved in 360 ml methyl isobutyl ketone. This solution is clarified by filtration and the clear solution is well stirred and heated to 60° C. At this temperature 2 g (5 mol%) of sertraline hydrochloride Form II are added after which directly the addition of the aqueous hydrogenchloride solution (37%) is started until pH<5. The resulting white suspension is cooled to 20° C. and sertraline hydrochloride is isolated by filtration and dried in vacuum. The sertraline is obtained as Form II.

EXAMPLE 13

Preparation of Polymorphic Form V 1 g of sertraline hydrochloride ethanol solvate is dried in vacuum (ca. 100 mbar) at 70° C. for 12 h.

Raman and X-ray powder diffraction studies show the product to be polymorphic form V (see FIGS. 5 and 6).

Figure 1:
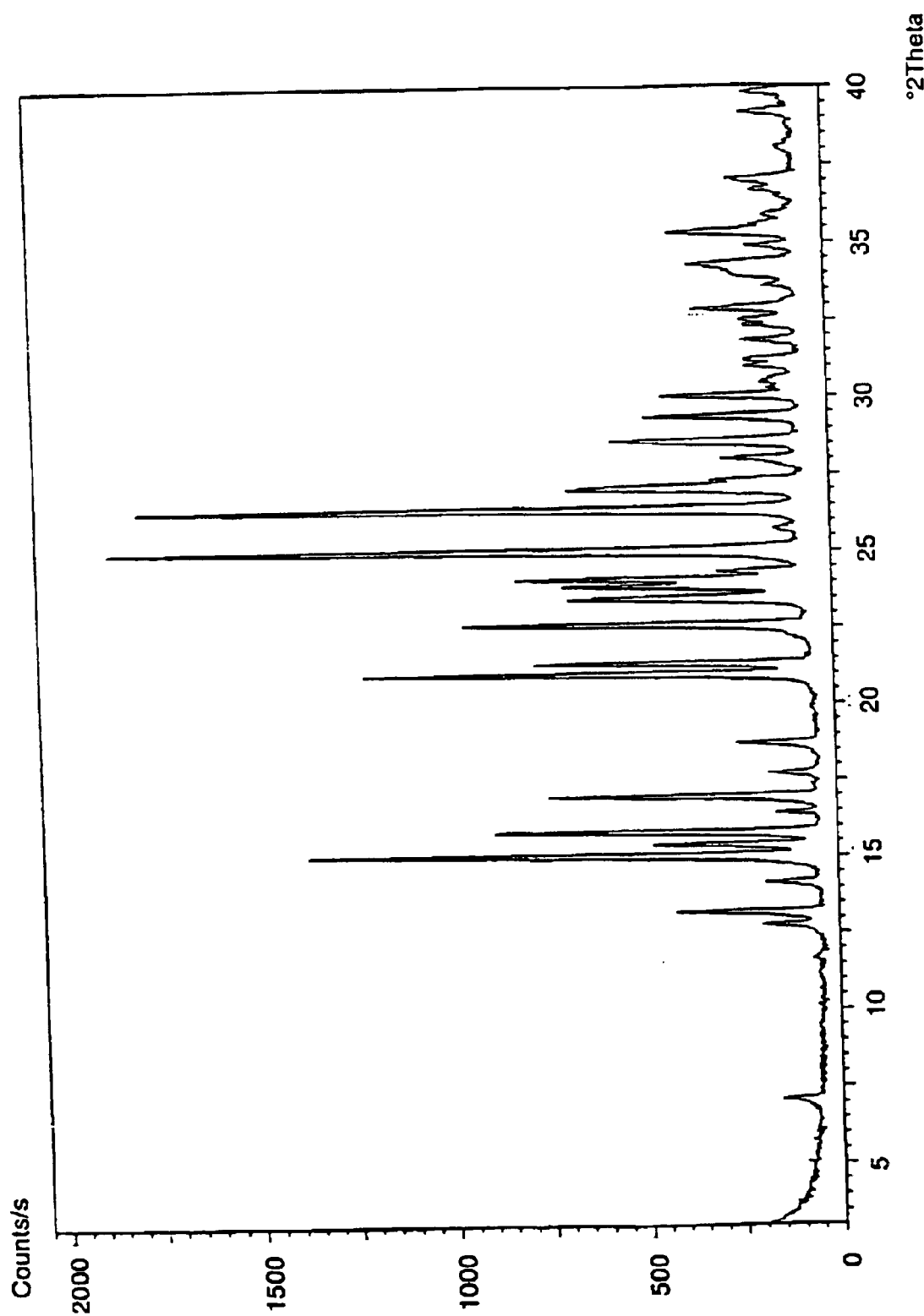
FIG. 1 is a characteristic X-ray powder diffraction pattern for polymorphic form I
Figure 2:
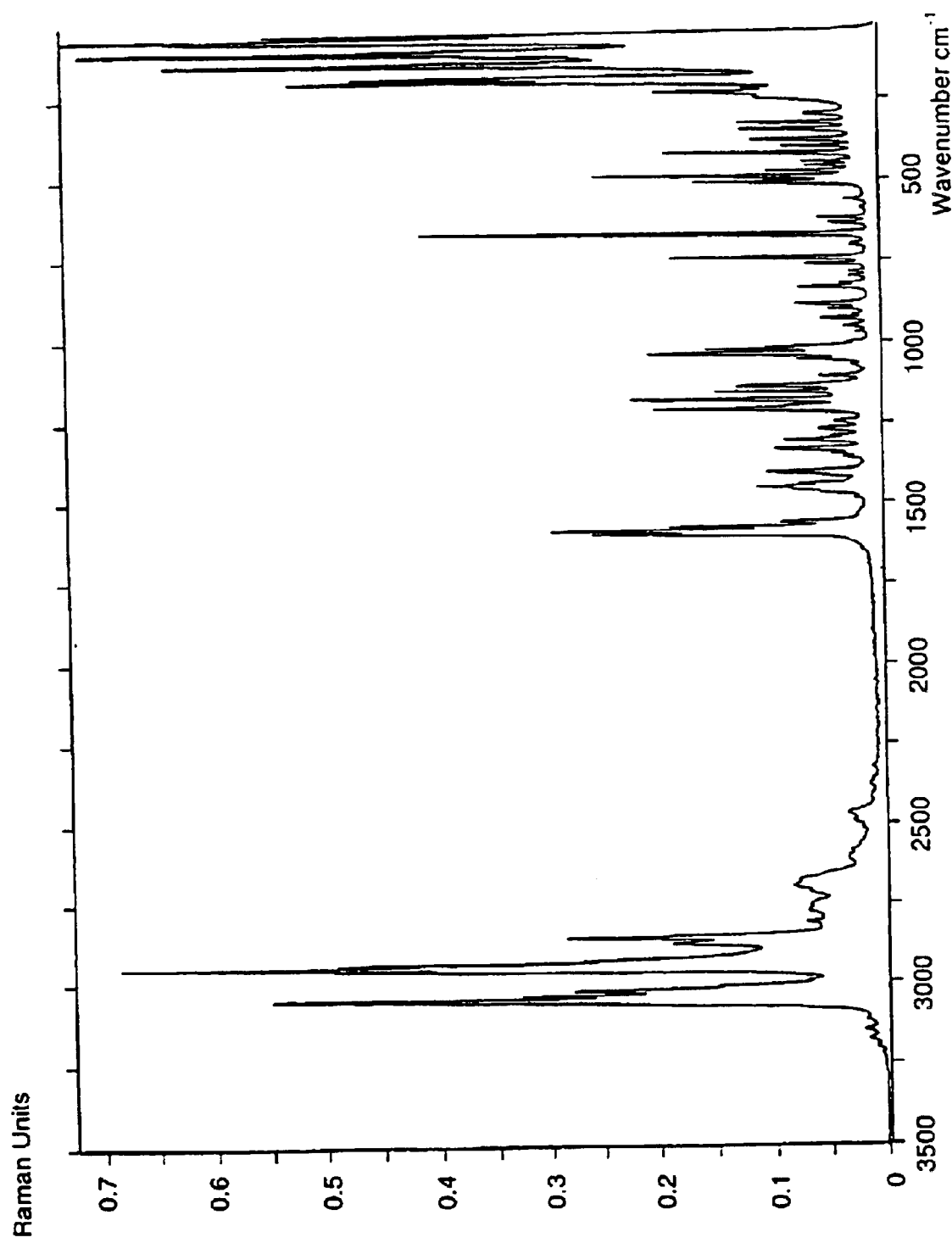
FIG. 2 is a characteristic Raman spectrum of polymorphic form I
Figure 3:
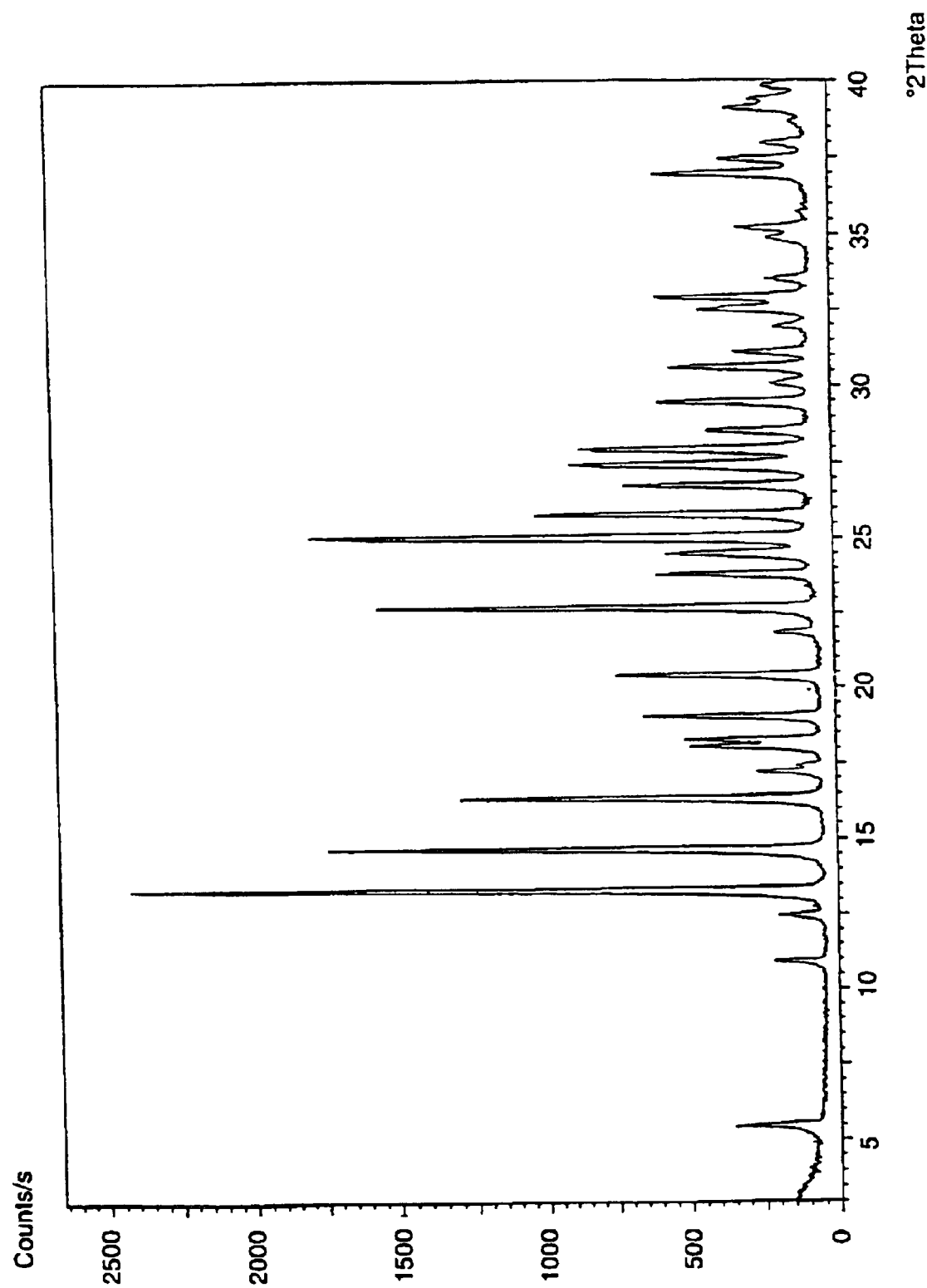
FIG. 3 is a characteristic X-ray powder diffraction pattern for polymorphic form II
Figure 4:
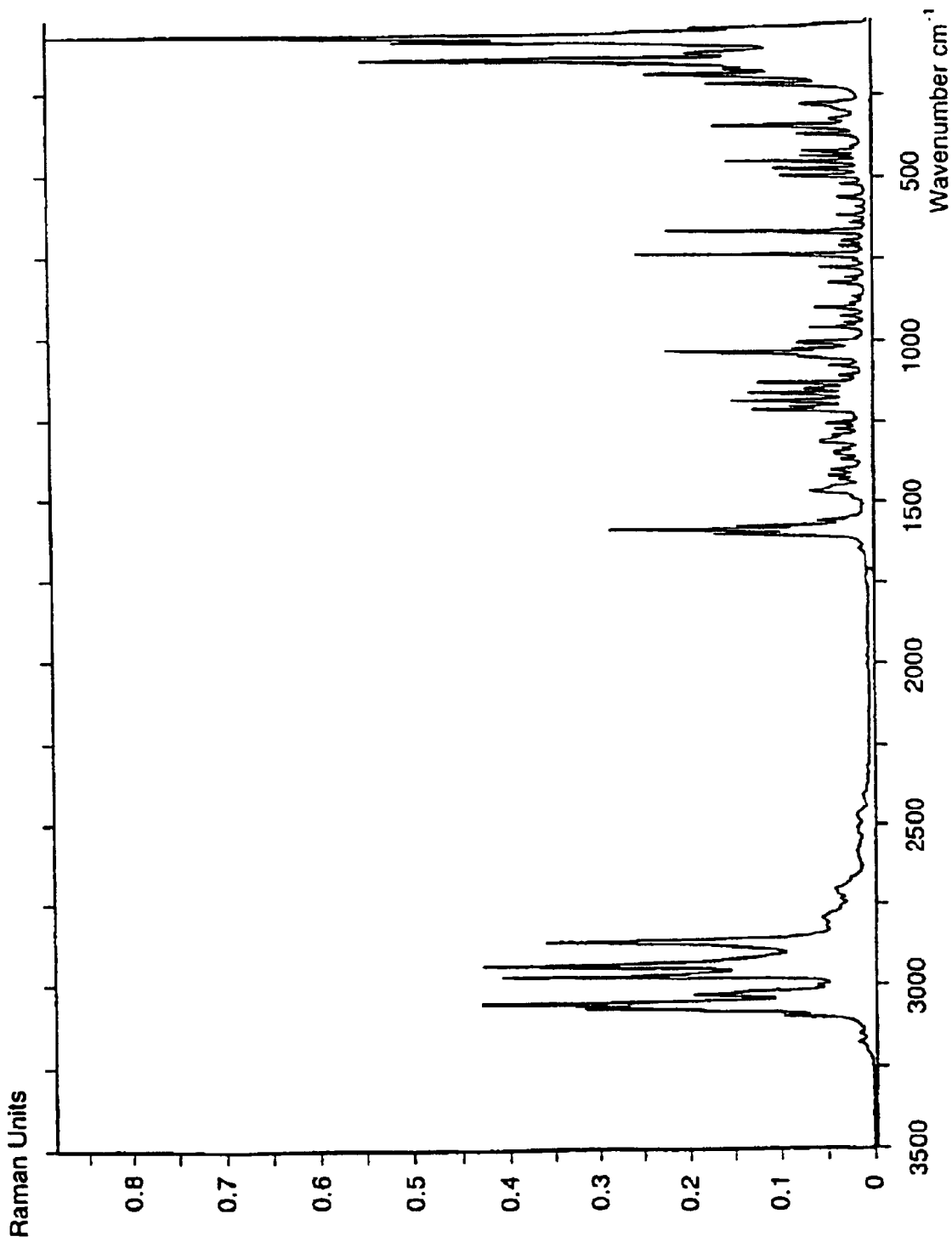
FIG. 4 is a characteristic Raman spectrum of polymorphic form II
Figure 5:
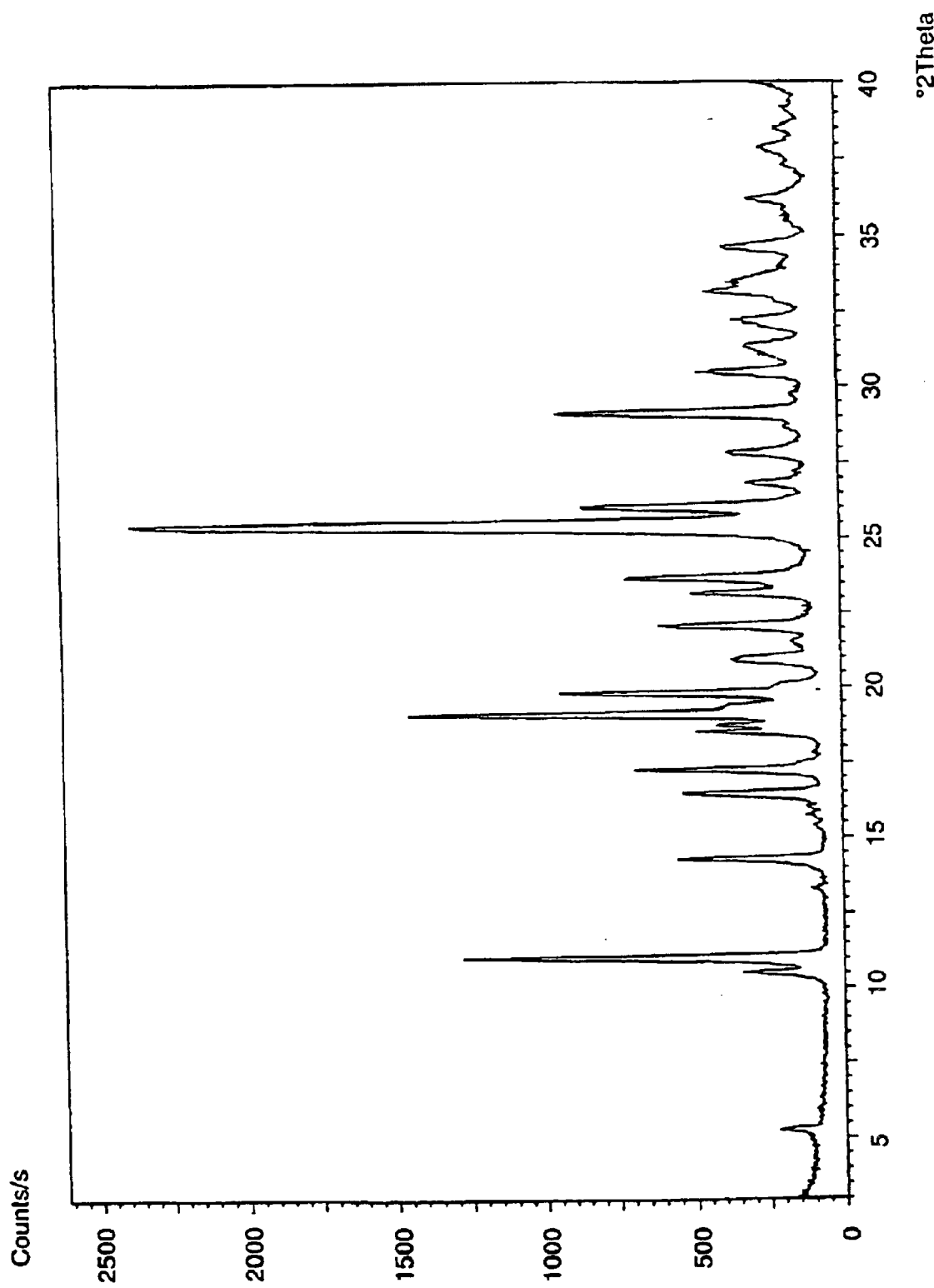
FIG. 5 is a characteristic X-ray powder diffraction pattern for polymorphic form V
Figure 6:
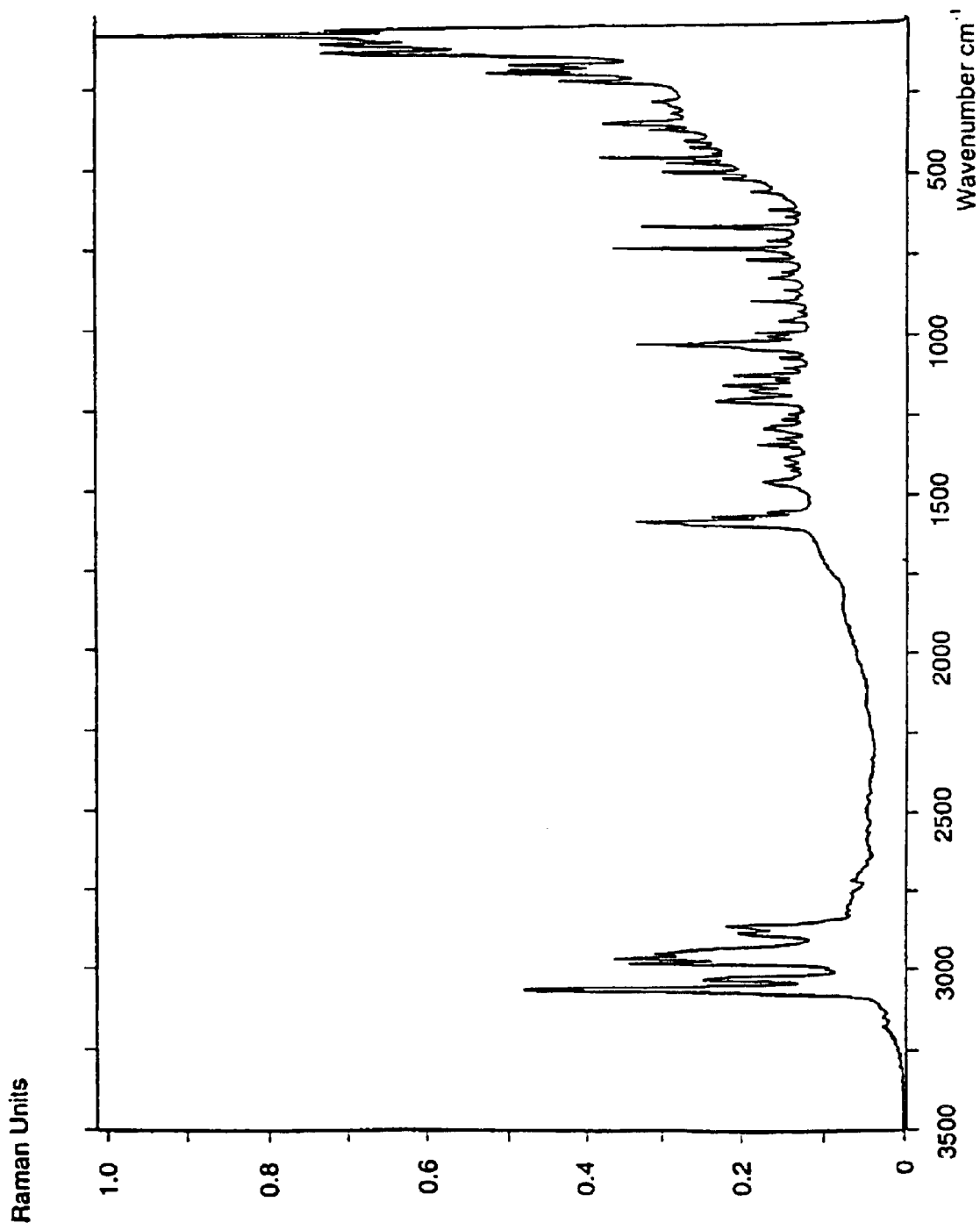
FIG. 6 is a characteristic Raman spectrum of polymorphic form V
Figure 7:
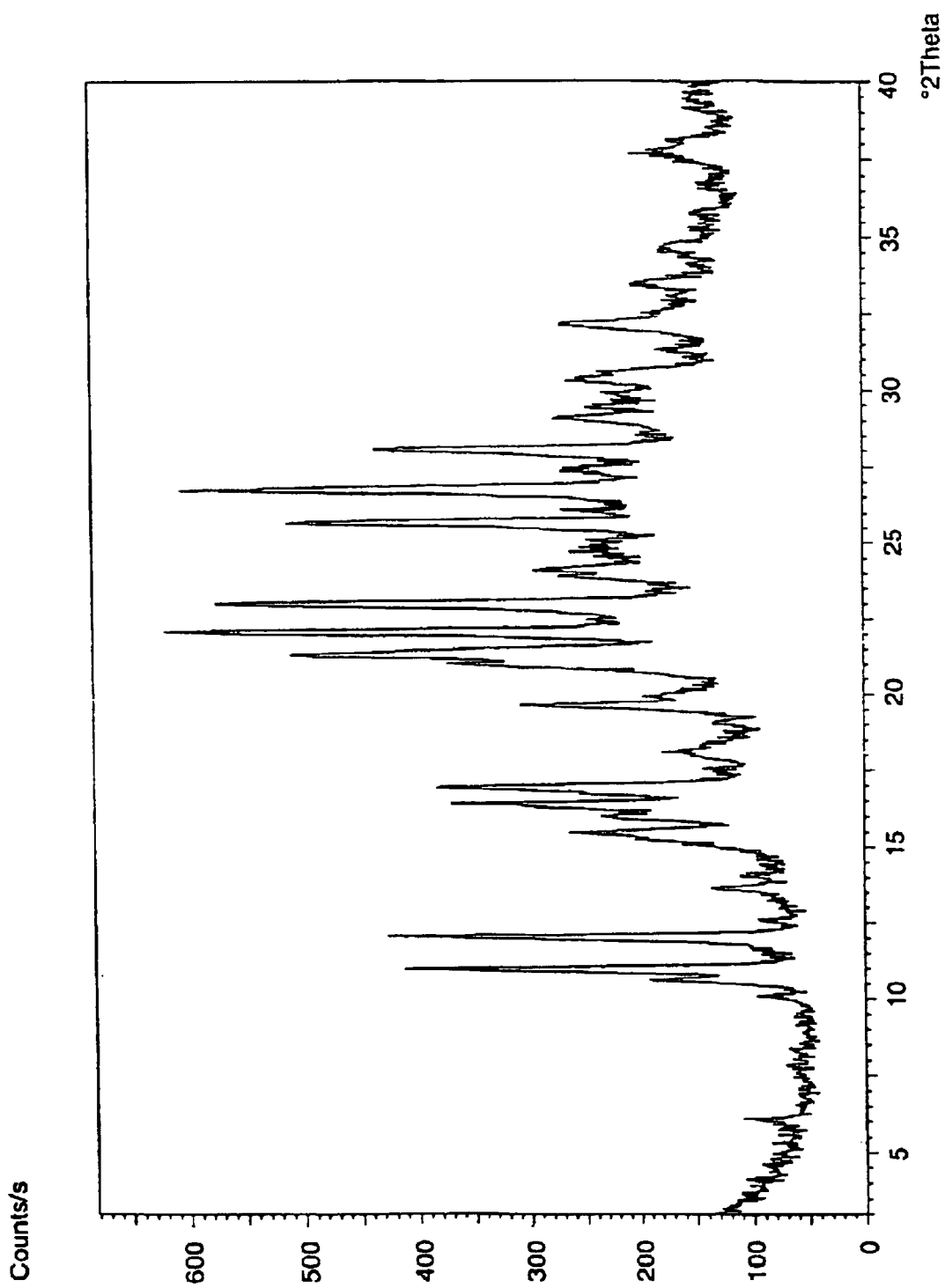
FIG. 7 is a characteristic X-ray powder diffraction pattern for polymorphic form T1
Figure 8:
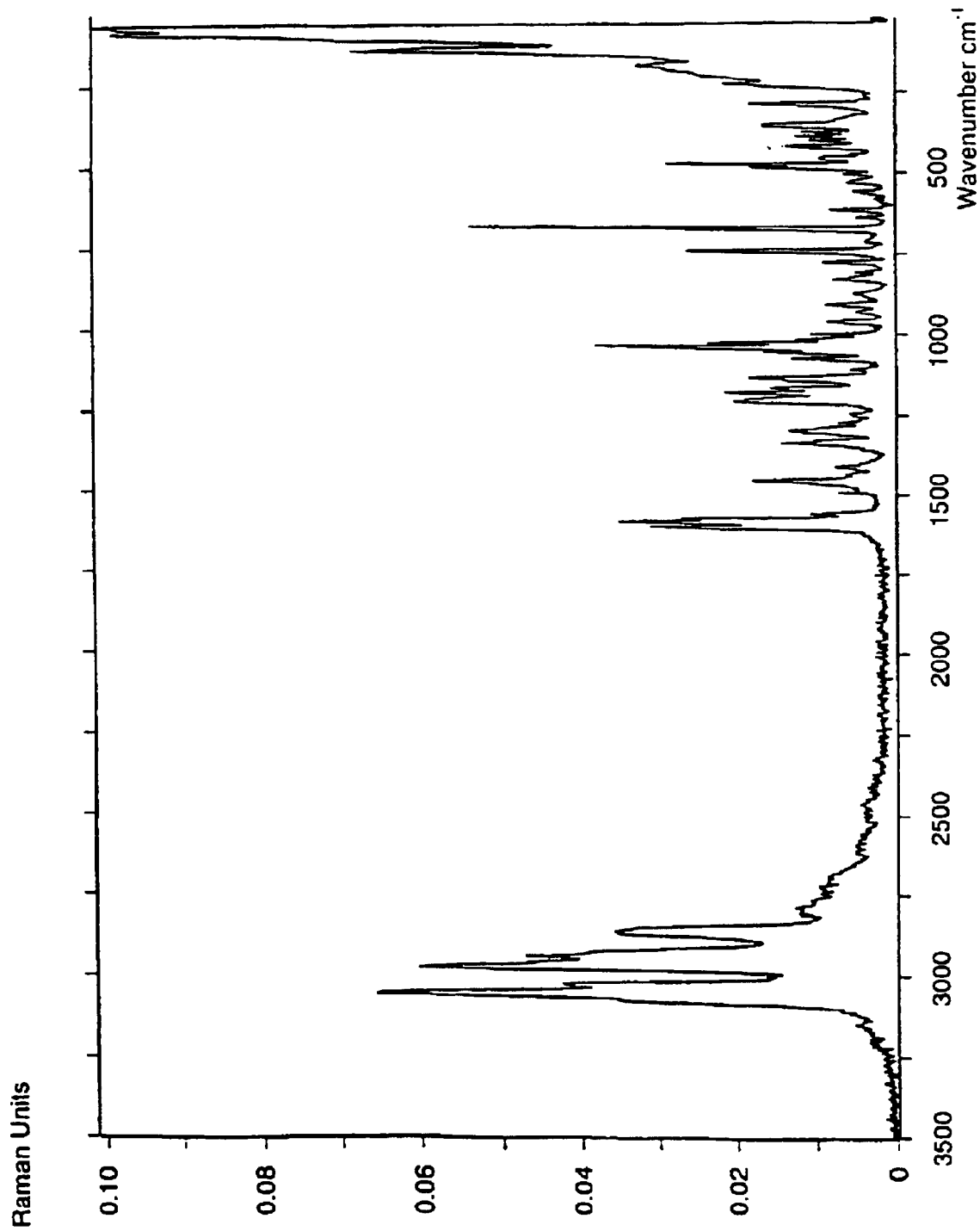
FIG. 8 is a characteristic Raman spectrum of polymorphic form T1
Figure 9:
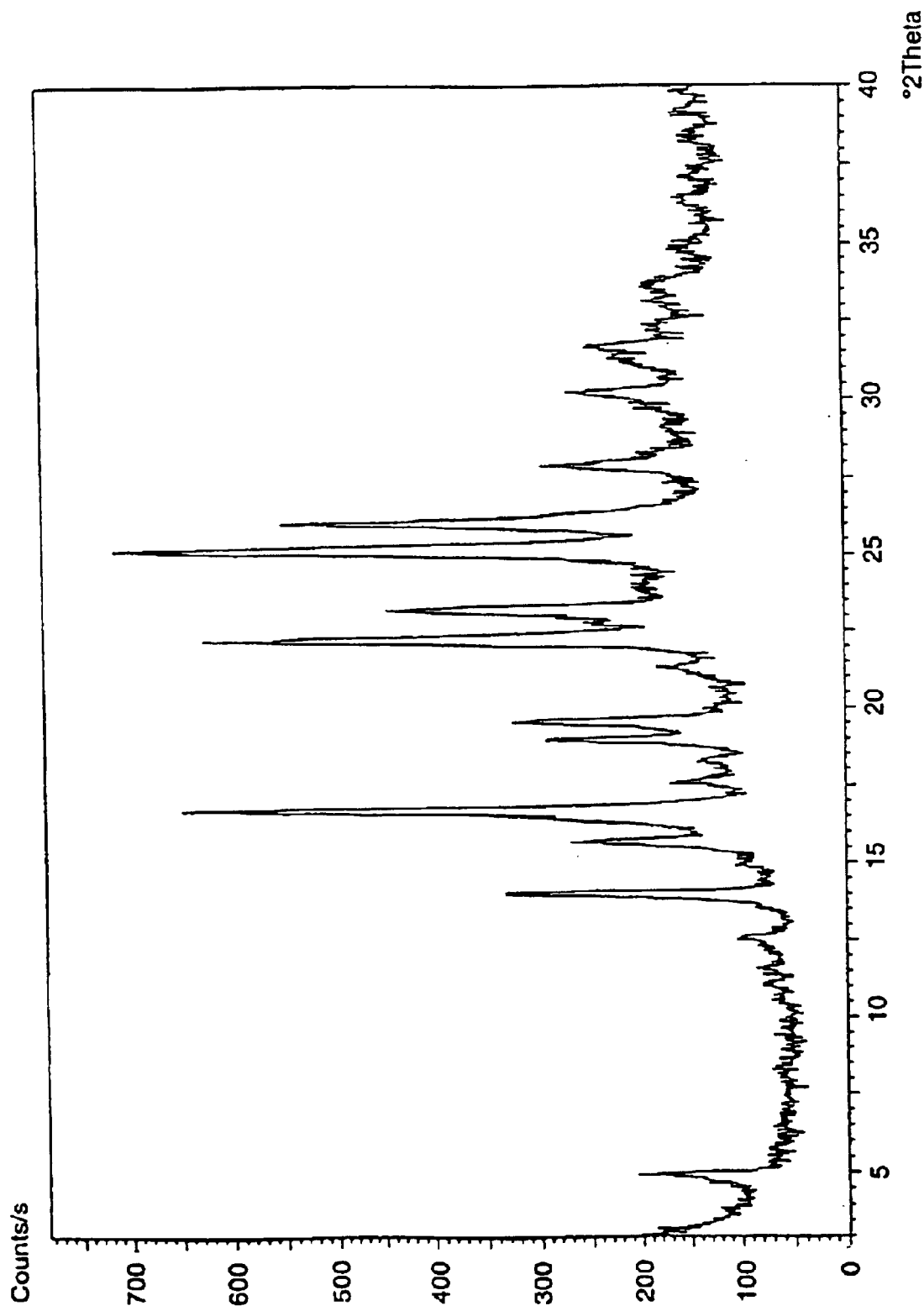
FIGS. 9, 10, 11, and 12 are characteristic X-ray powder diffraction patterns for different hydrates with varying amounts of water bonded in the crystal lattice, generally designated as polymorphic forms CSC1
Figure 10:
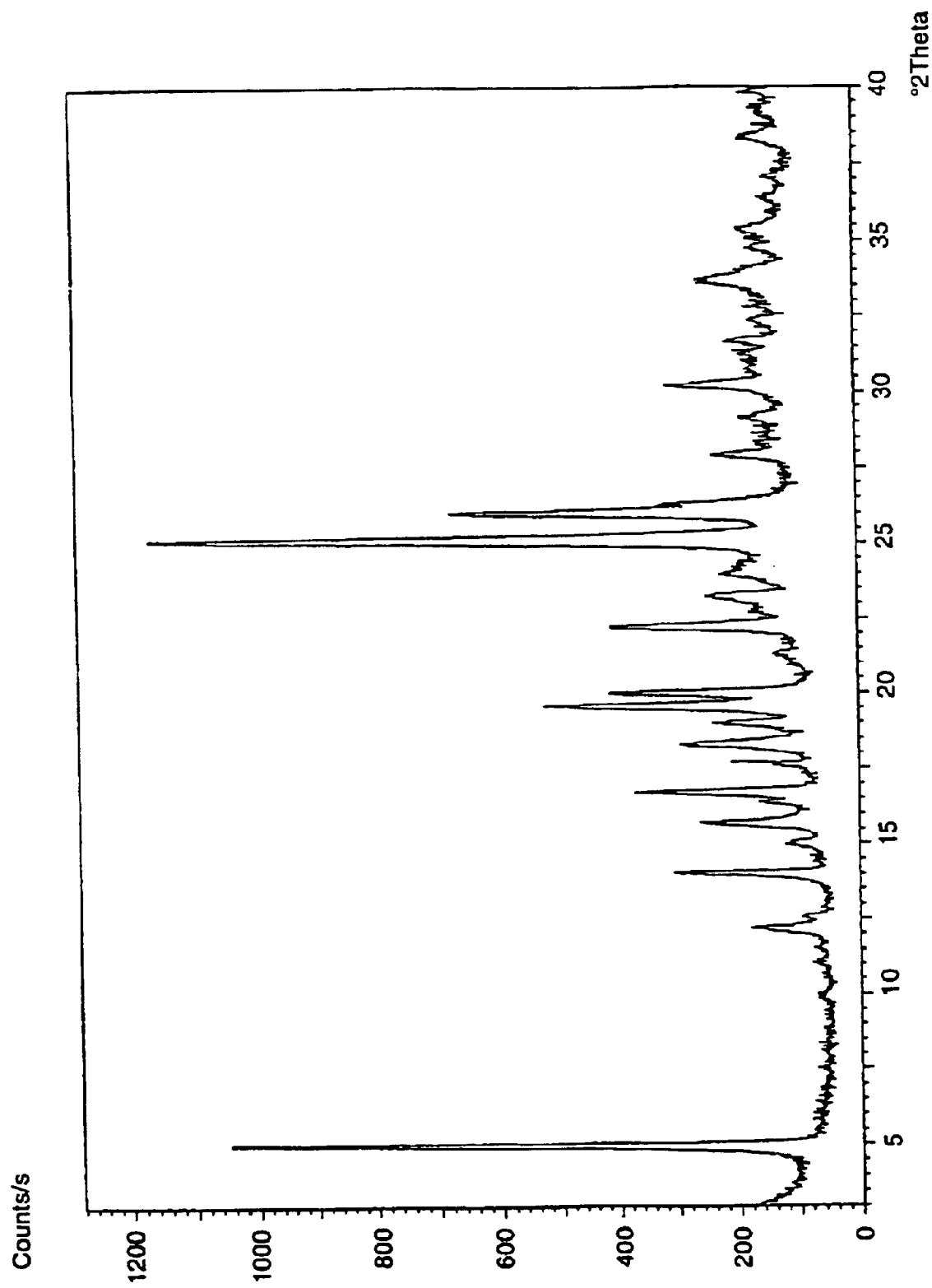
Figure 11:
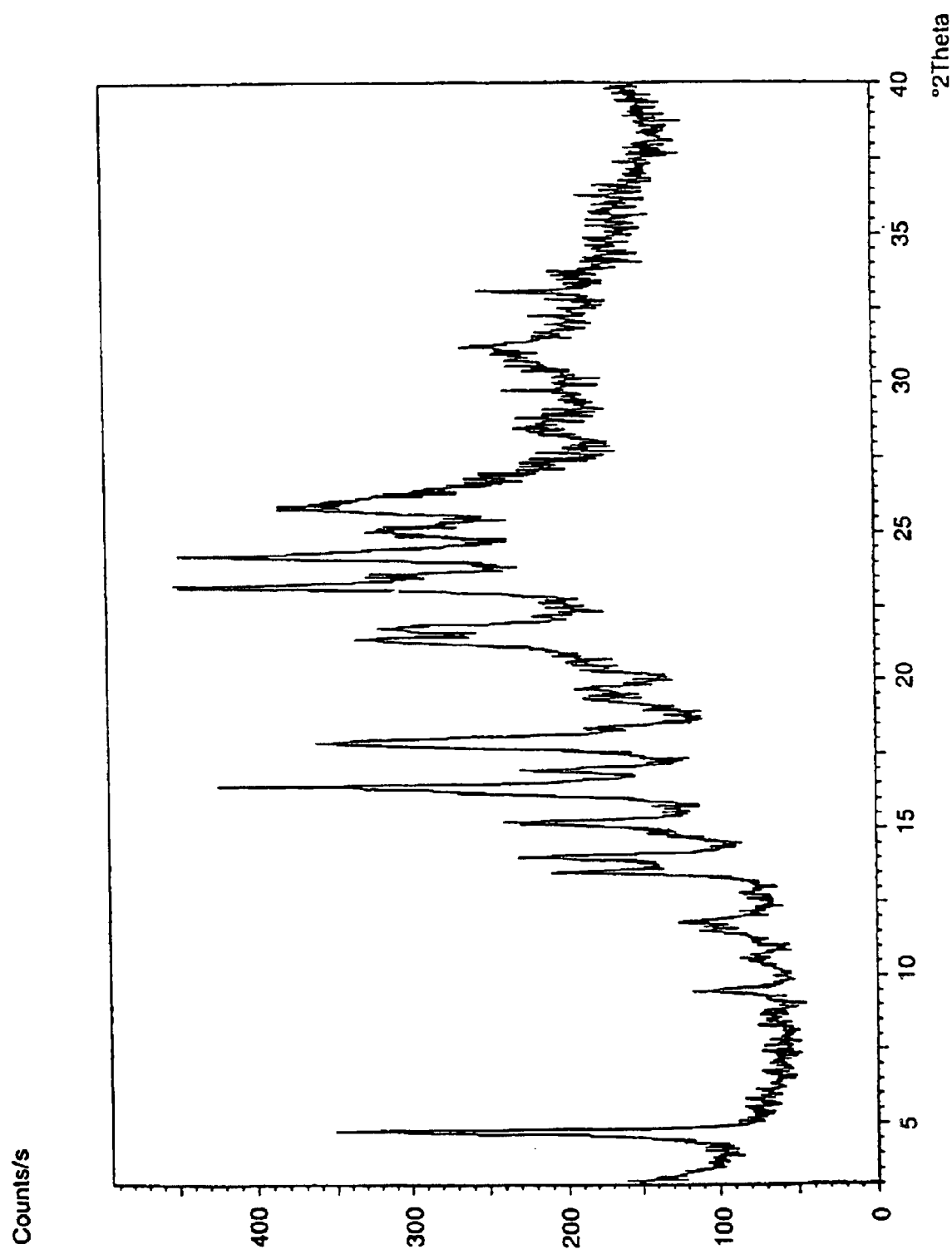
Figure 12:
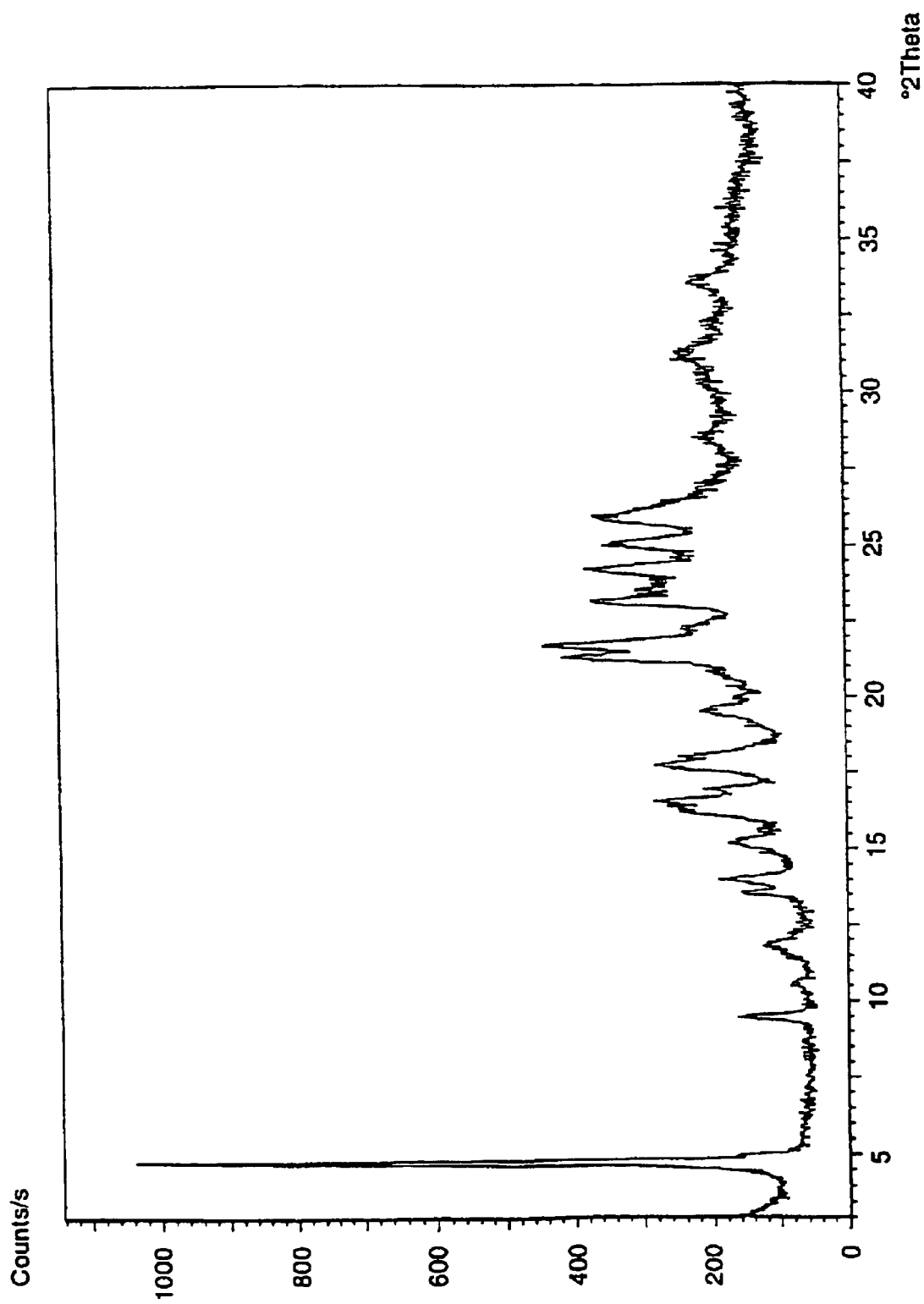
Figure 13:
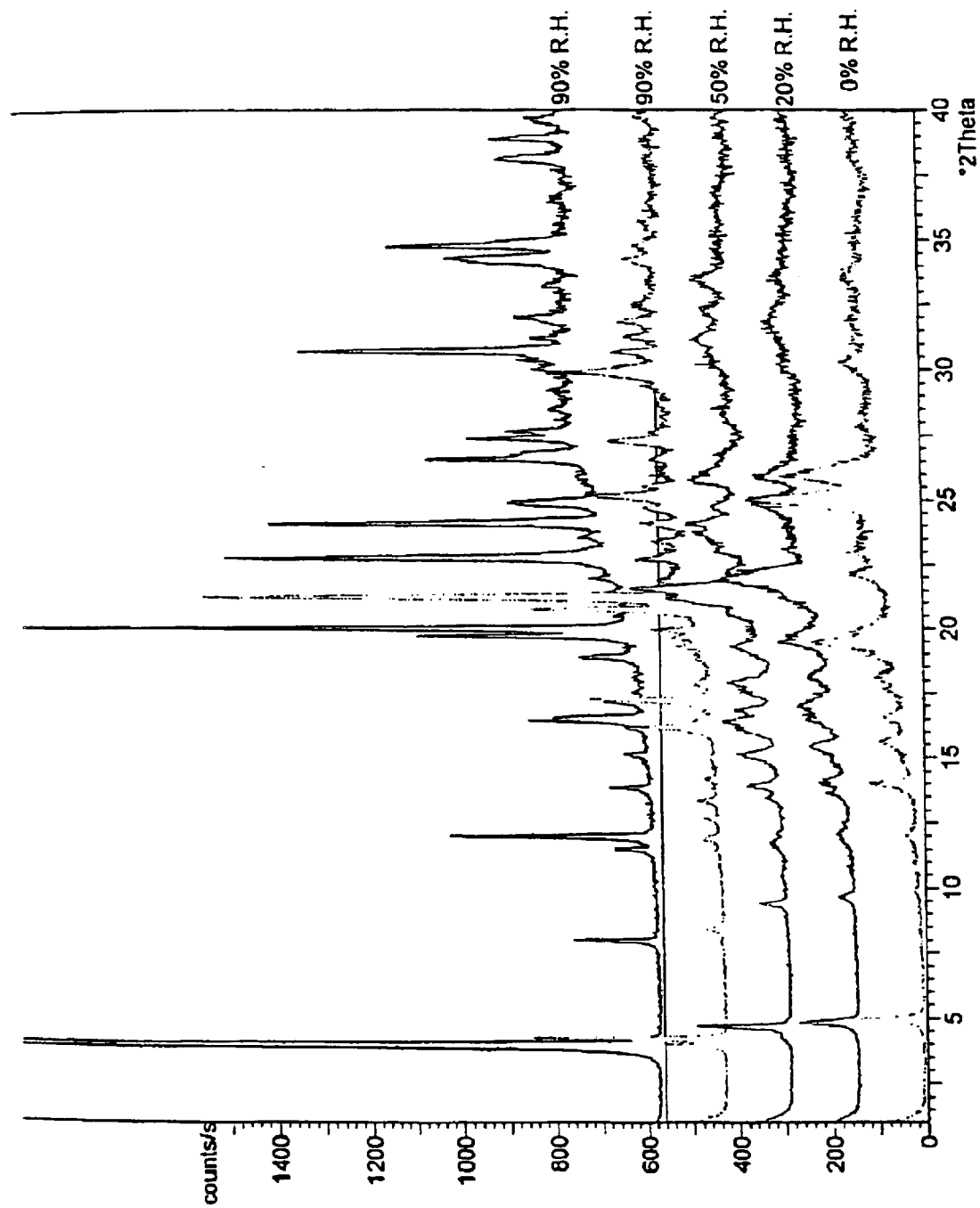
FIG. 13 is a plot of X-ray powder diffraction patterns for the hydrates at different levels of relative humidity
Figure 14:
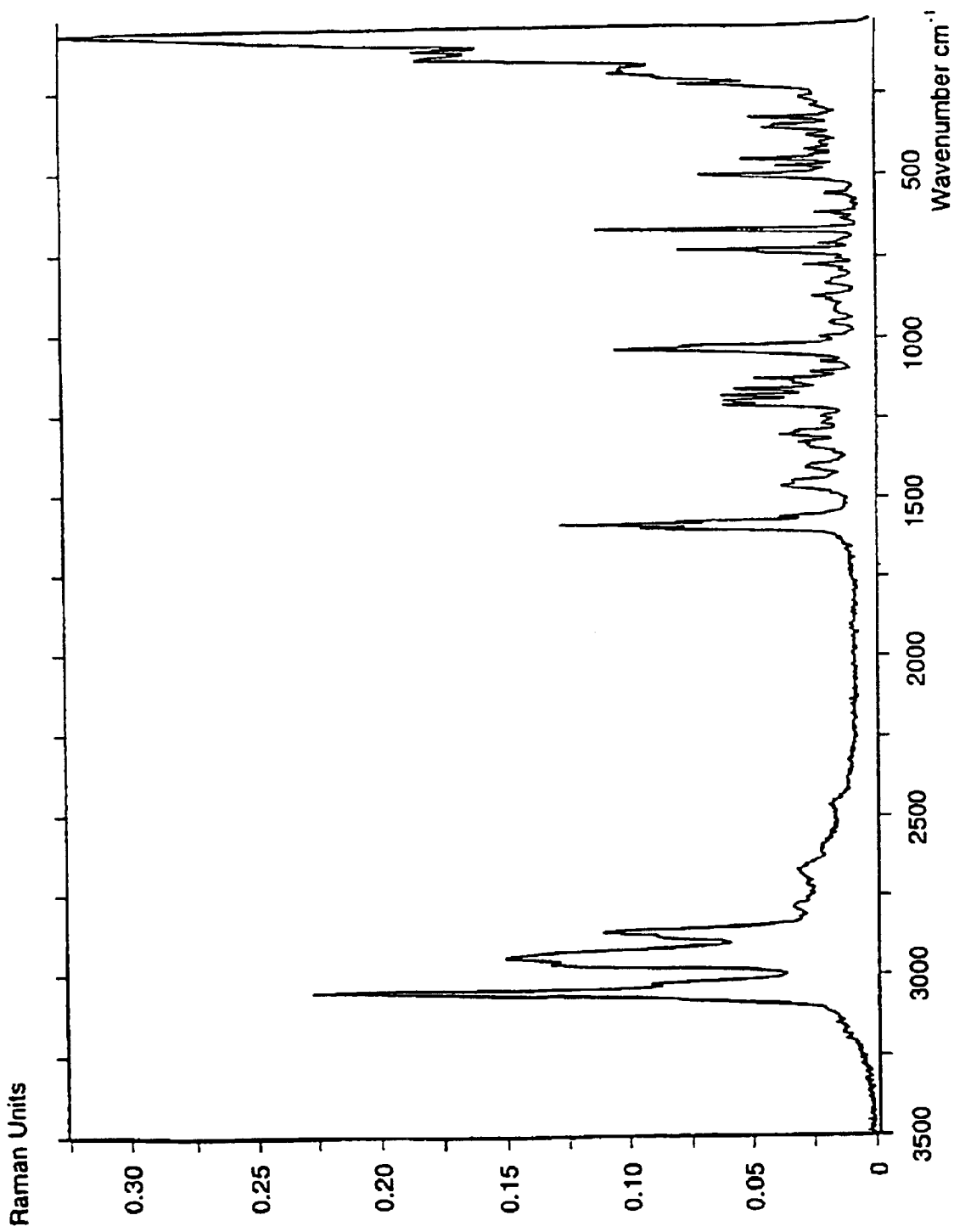
FIGS. 14, 15, 16, 17 and 18 are characteristic Raman spectra for different hydrates with varying amounts of water bonded in the crystal lattice, generally designated as polymorphic forms CSC1
Figure 15:
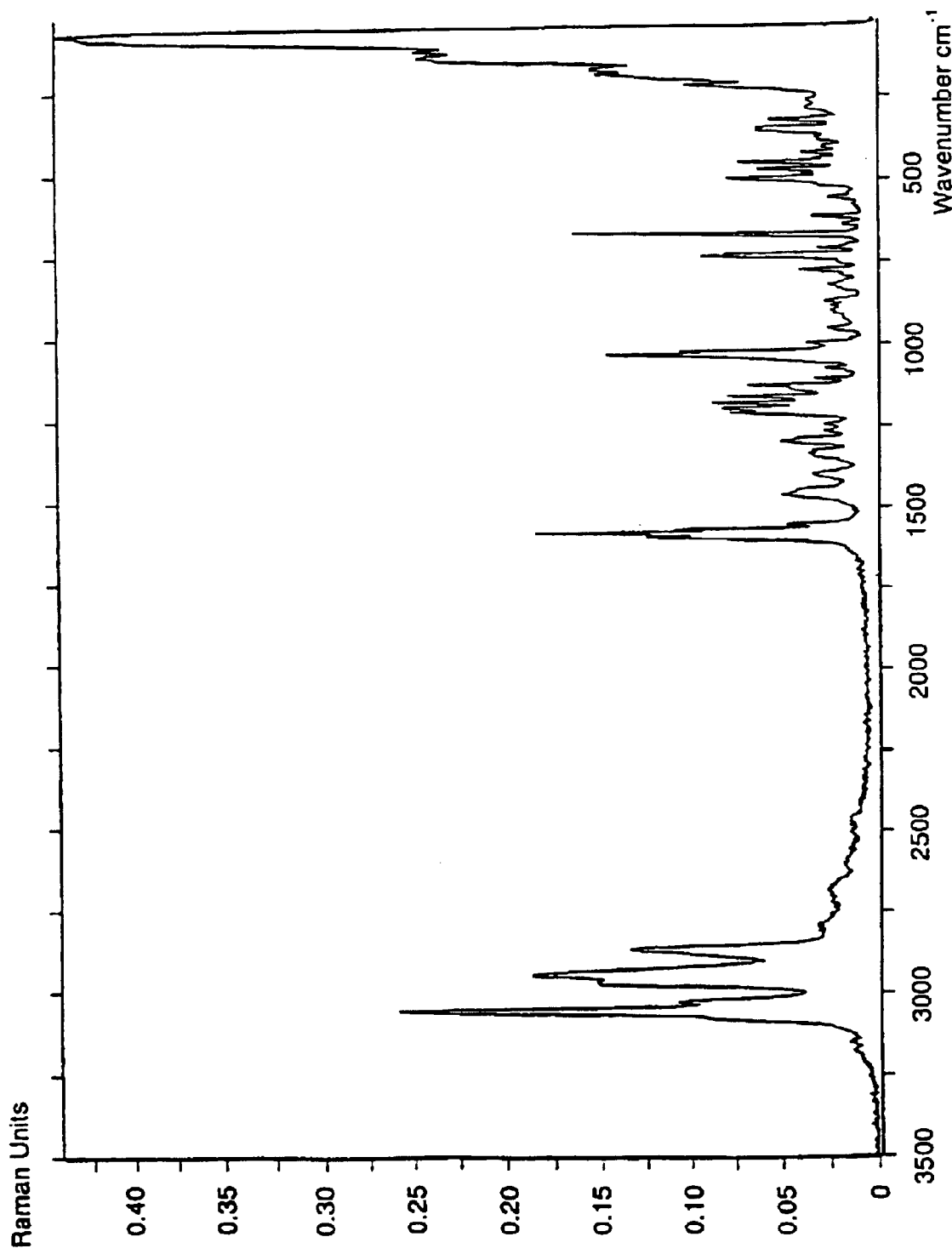
Figure 16:
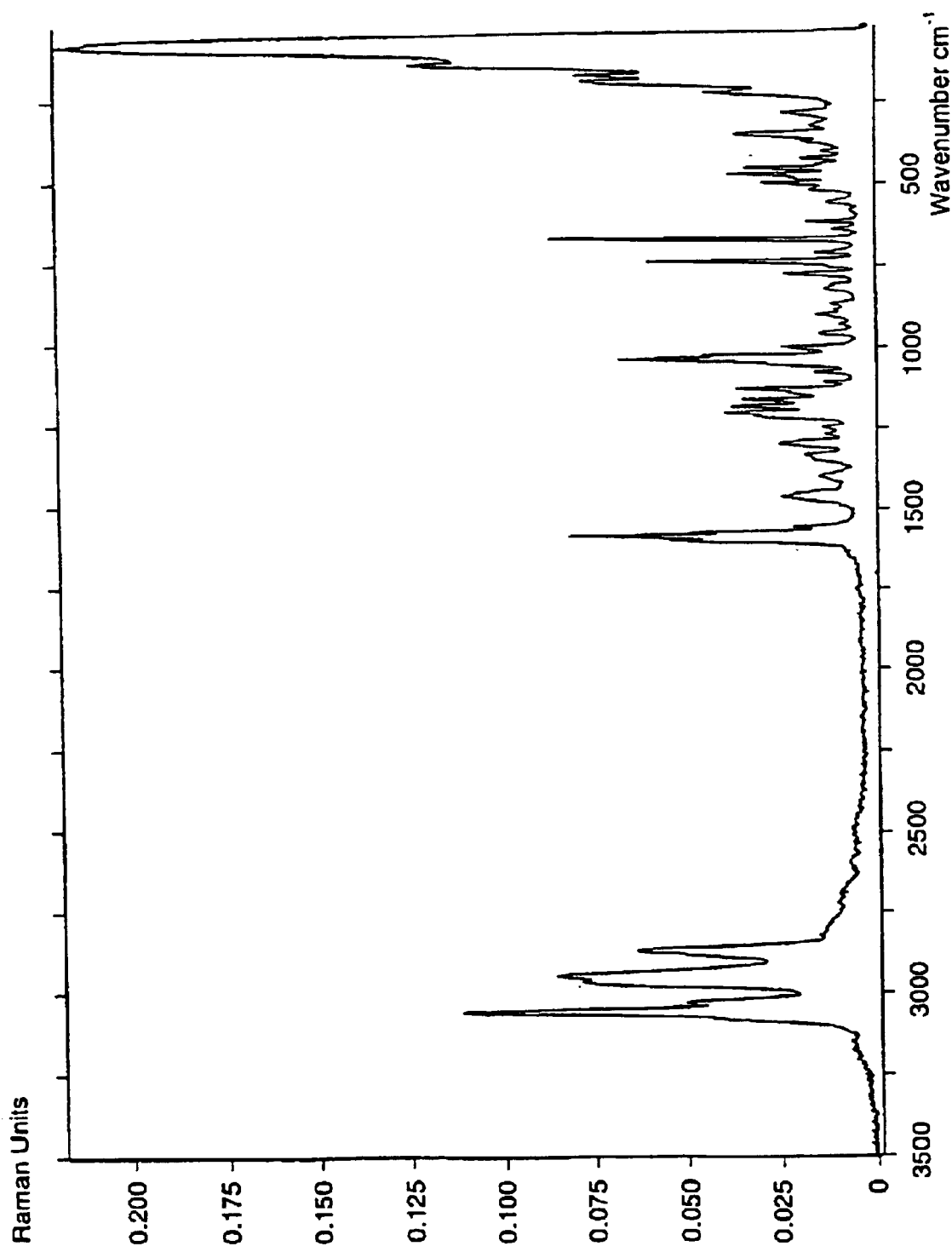
Figure 17:
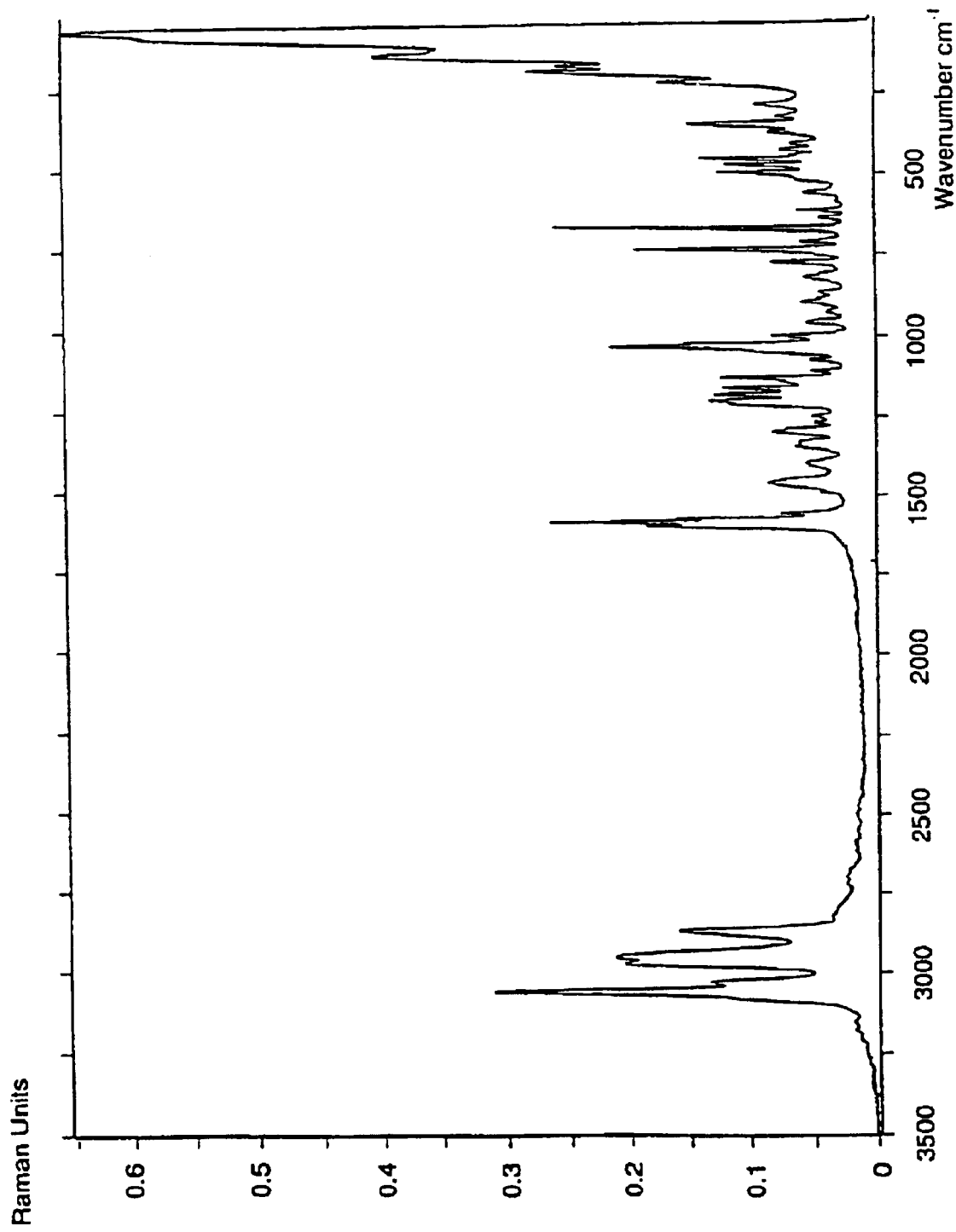
Figure 18:
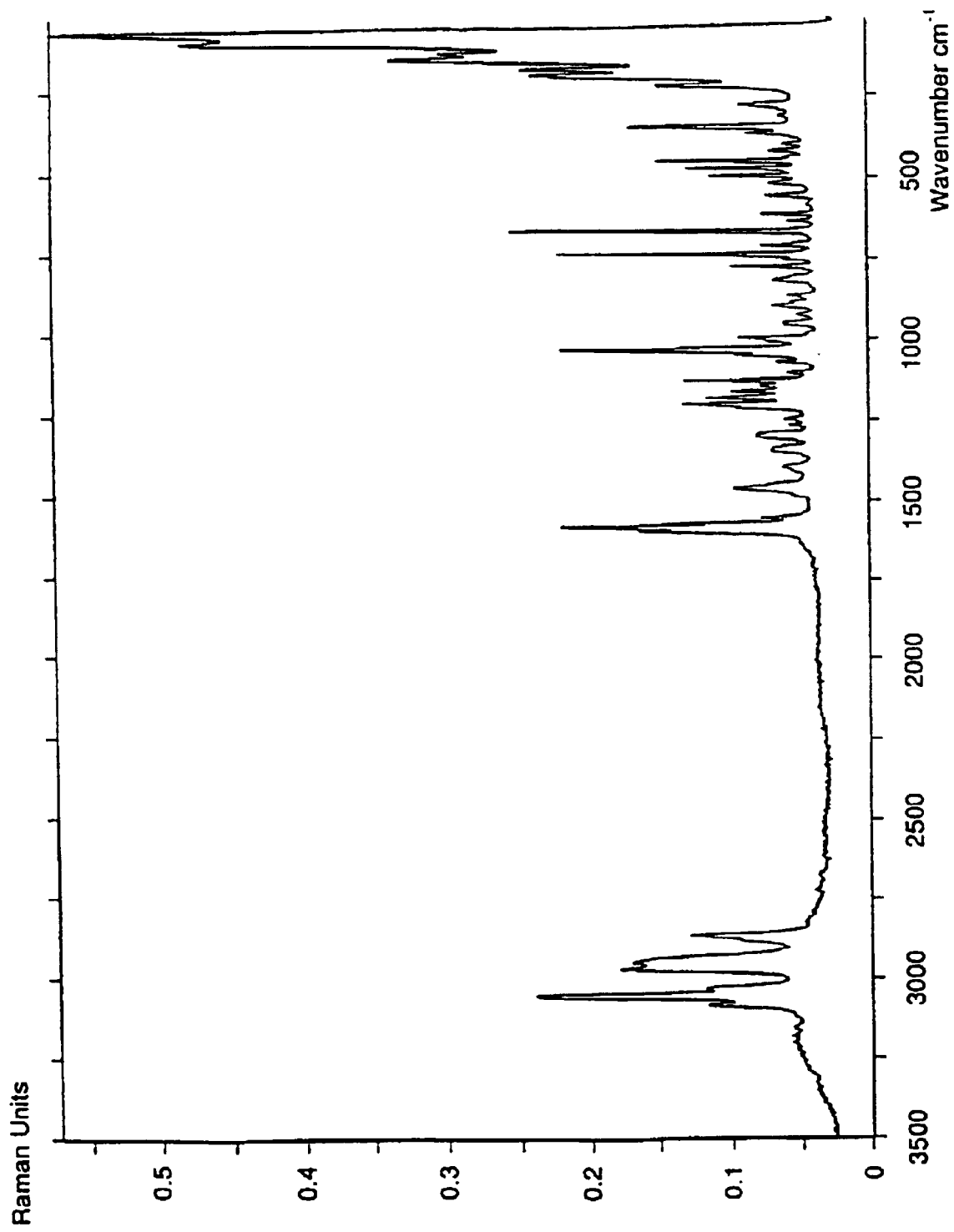
Figure 19:
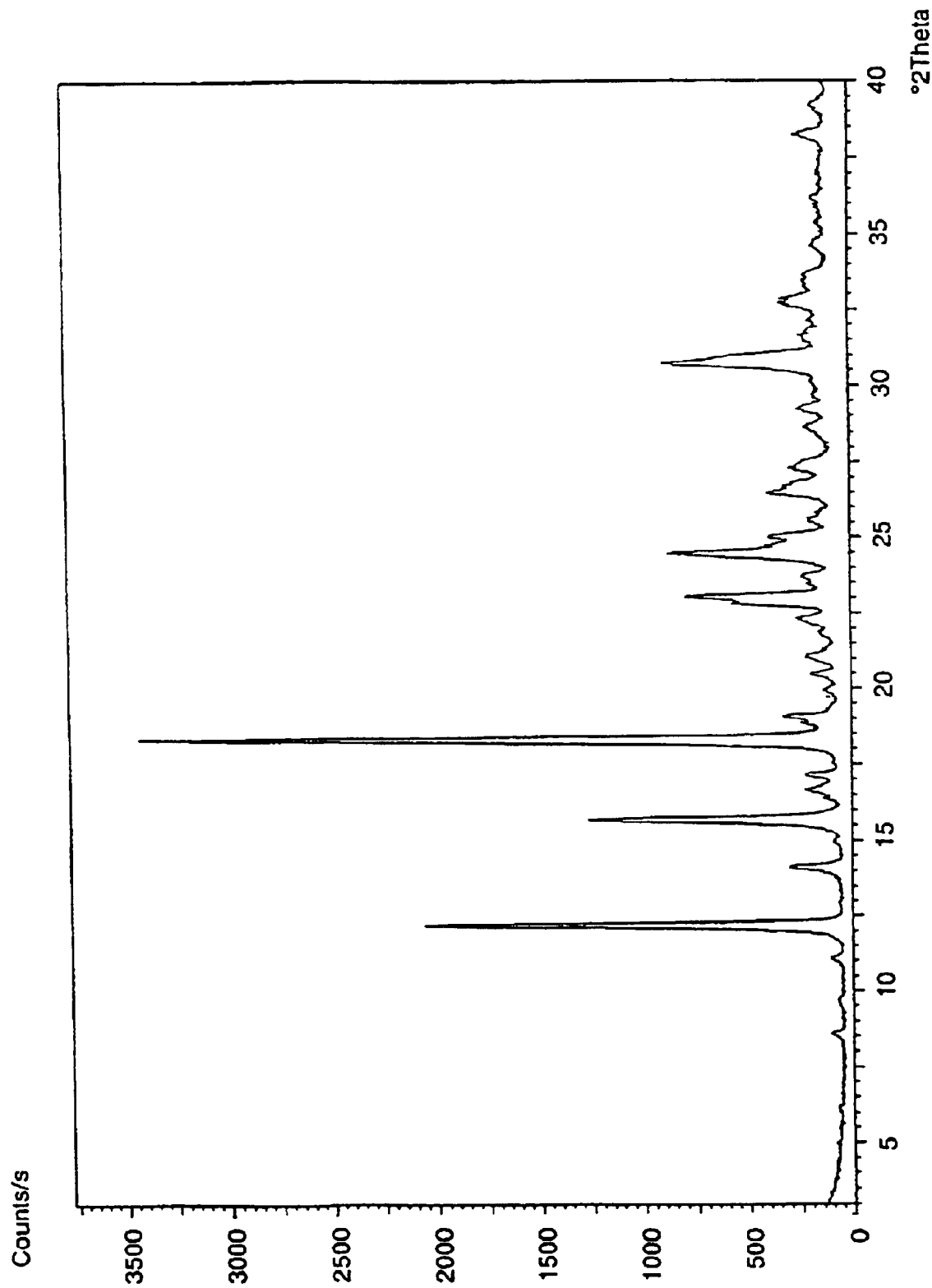
FIG. 19 is a characteristic X-ray powder diffraction pattern for polymorphic form CSC2
Figure 20:
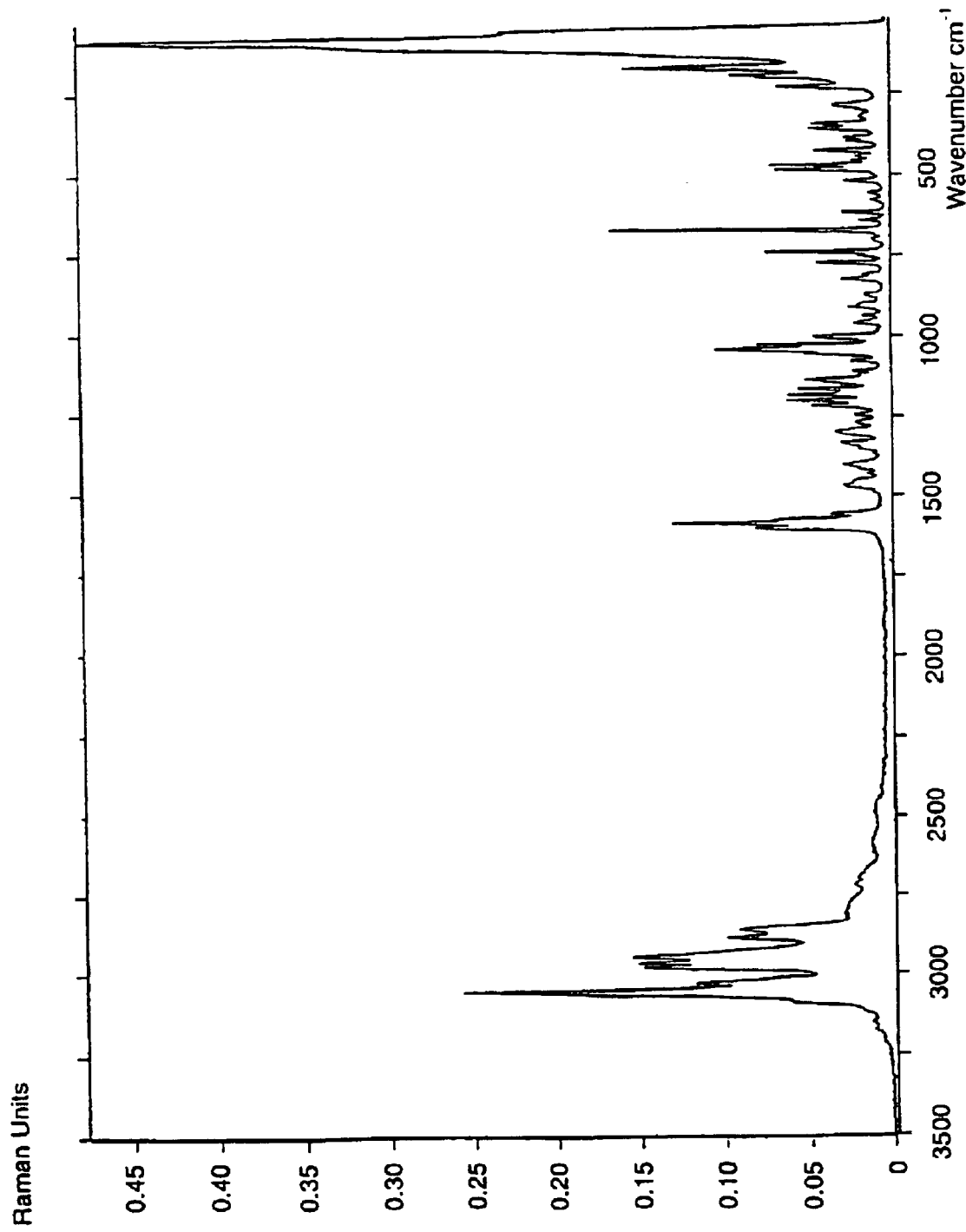
FIG. 20 is a characteristic Raman spectrum of polymorphic form CSC2
Figure 21:
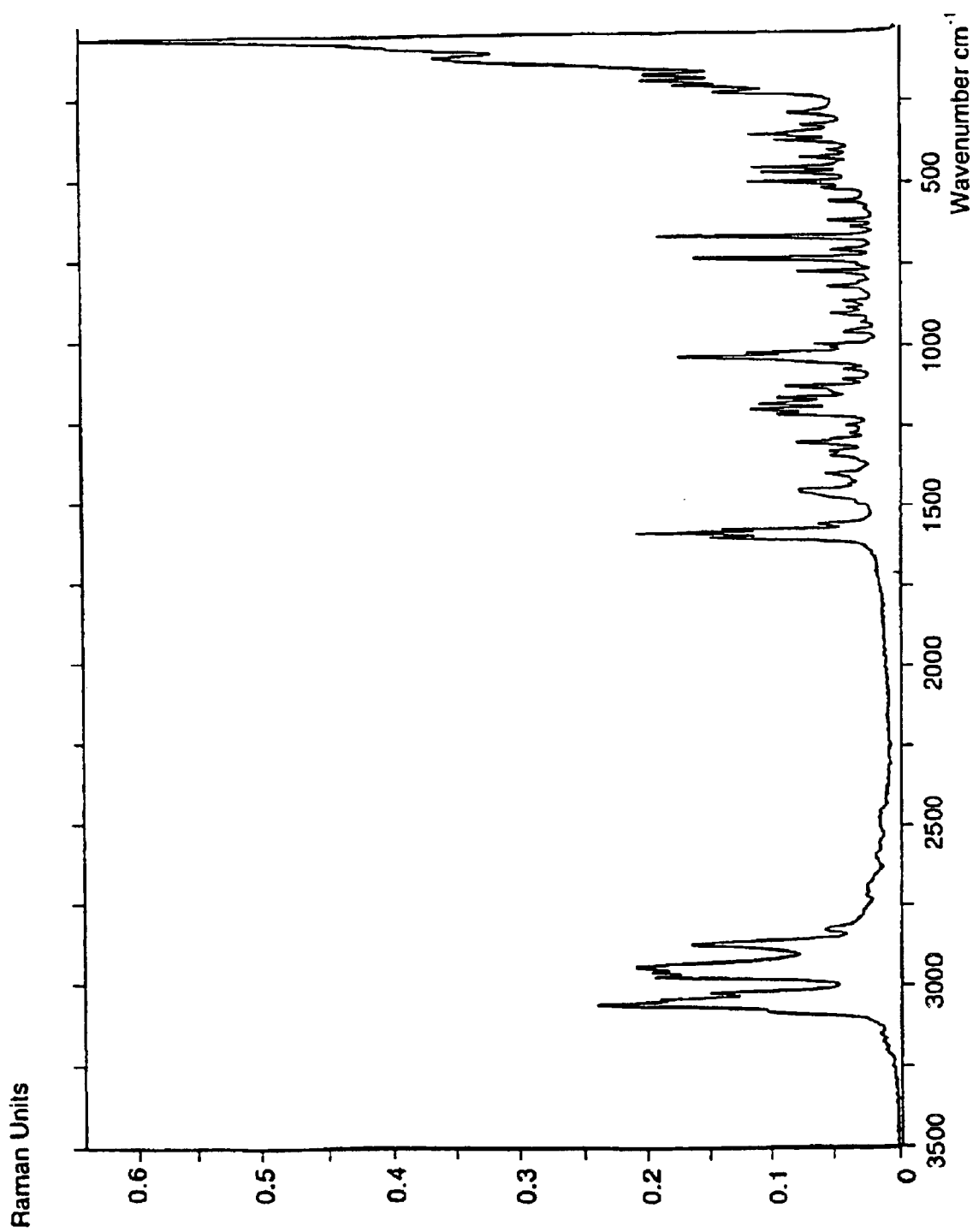
FIG. 21 is a characteristic Raman spectrum of the methanol solvate
Figure 22:
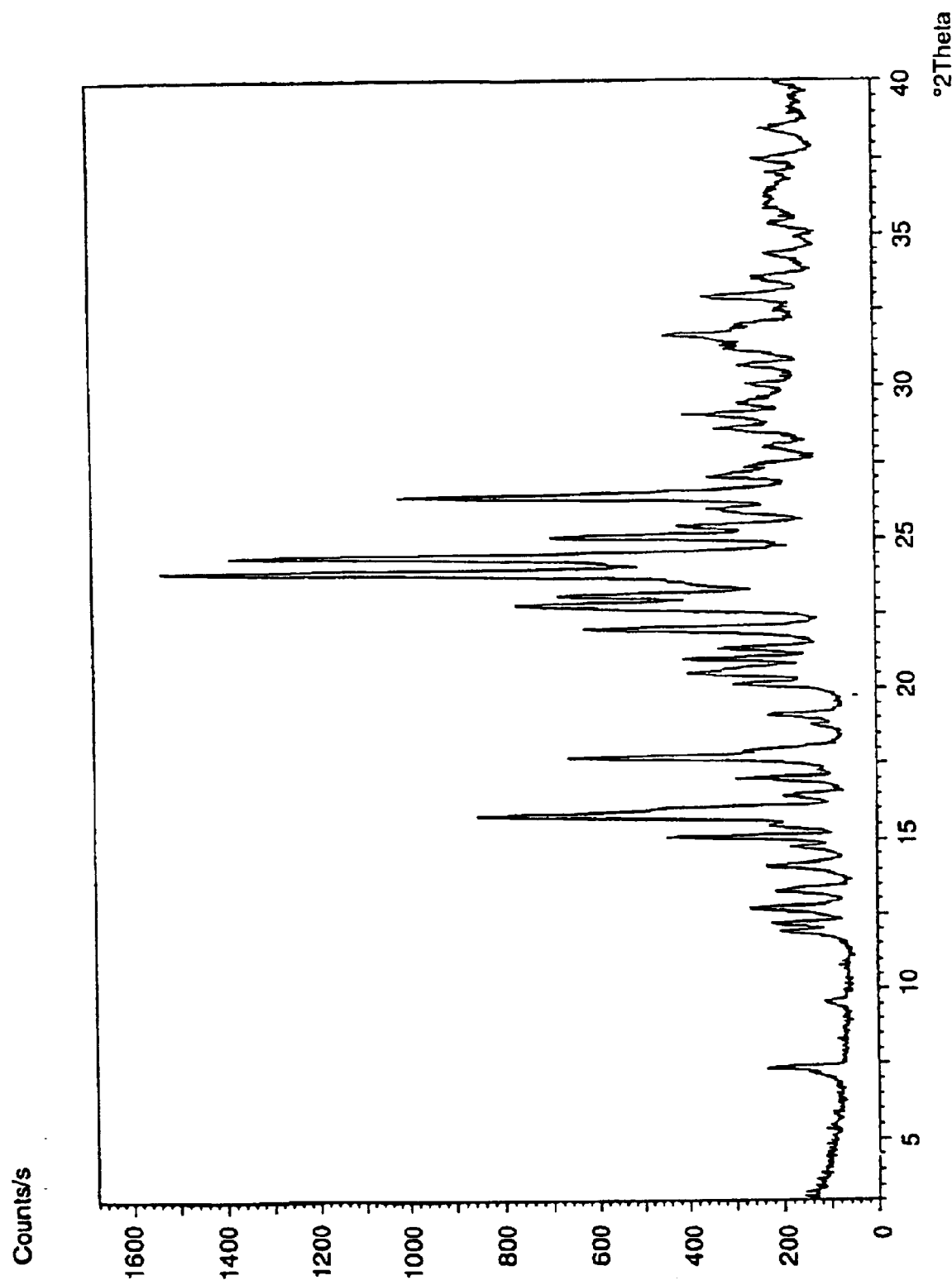
FIG. 22 is a characteristic X-ray powder diffraction pattern for the ethanol solvate
Figure 23:
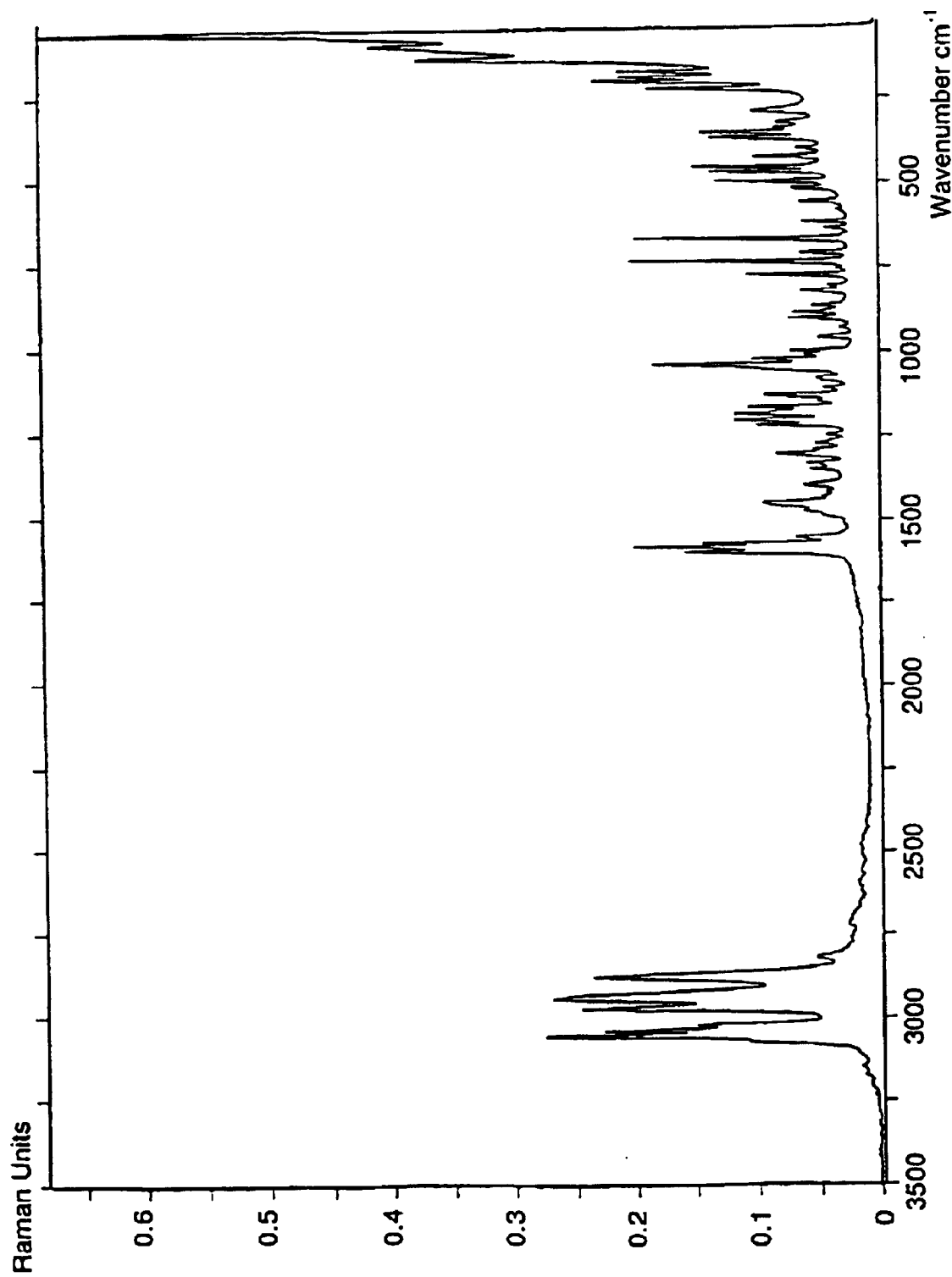
FIG. 23 is a characteristic Raman spectrum of the ethanol solvate
Figure 24:
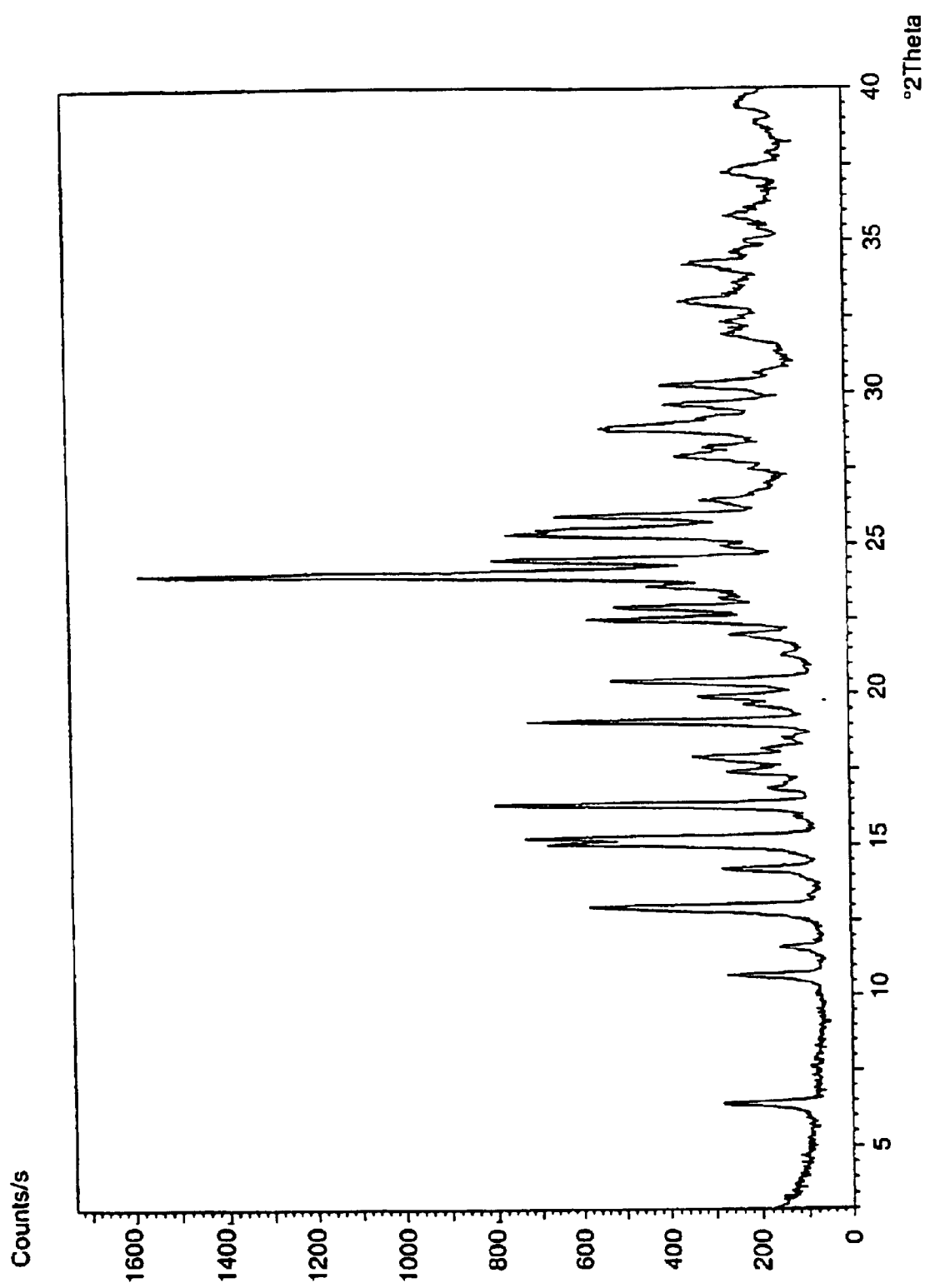
FIG. 24 is a characteristic X-ray powder diffraction pattern for the isopropanol solvate
Figure 25:
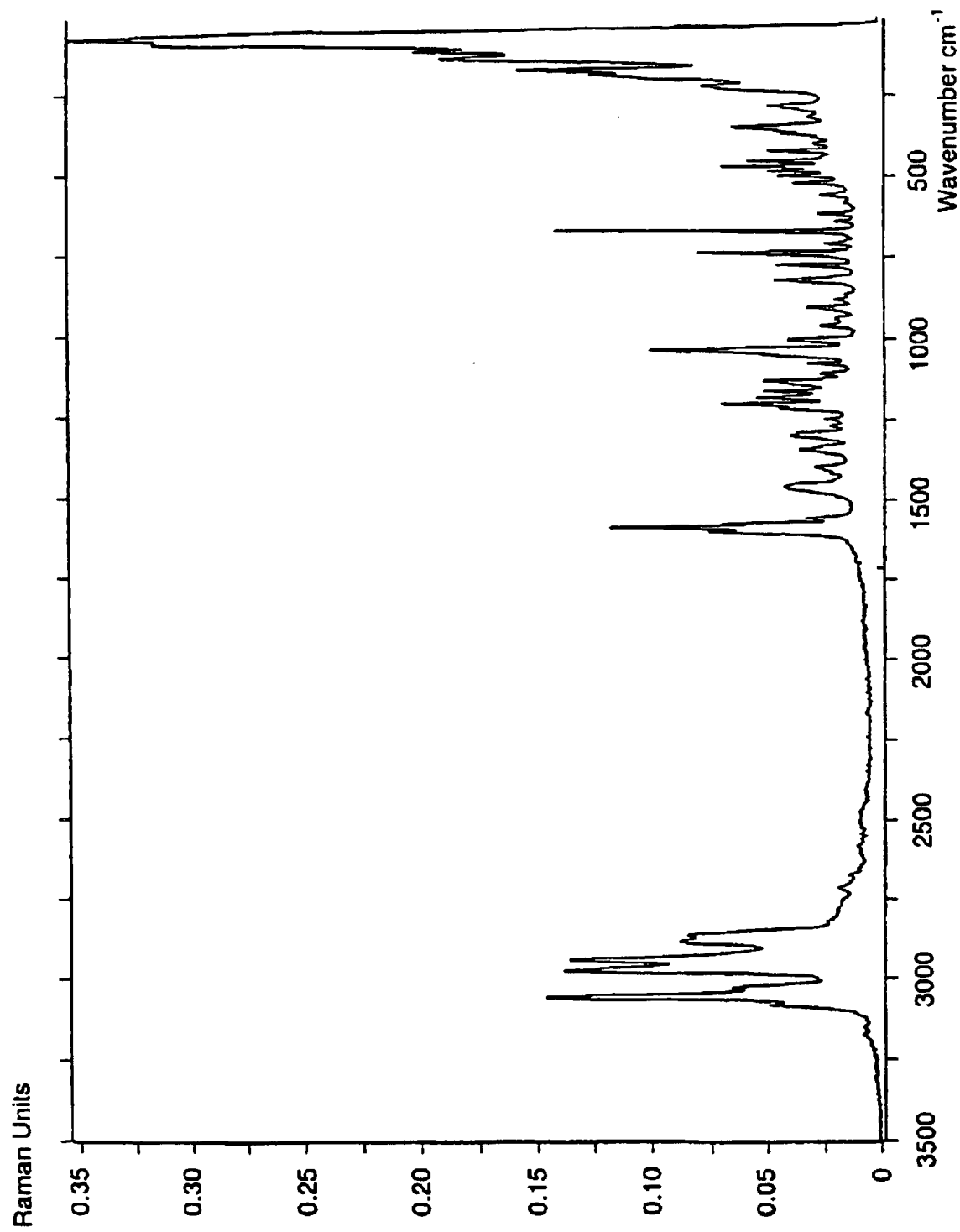
FIG. 25 is a characteristic Raman spectrum of the isopropanol solvate
Figure 26:
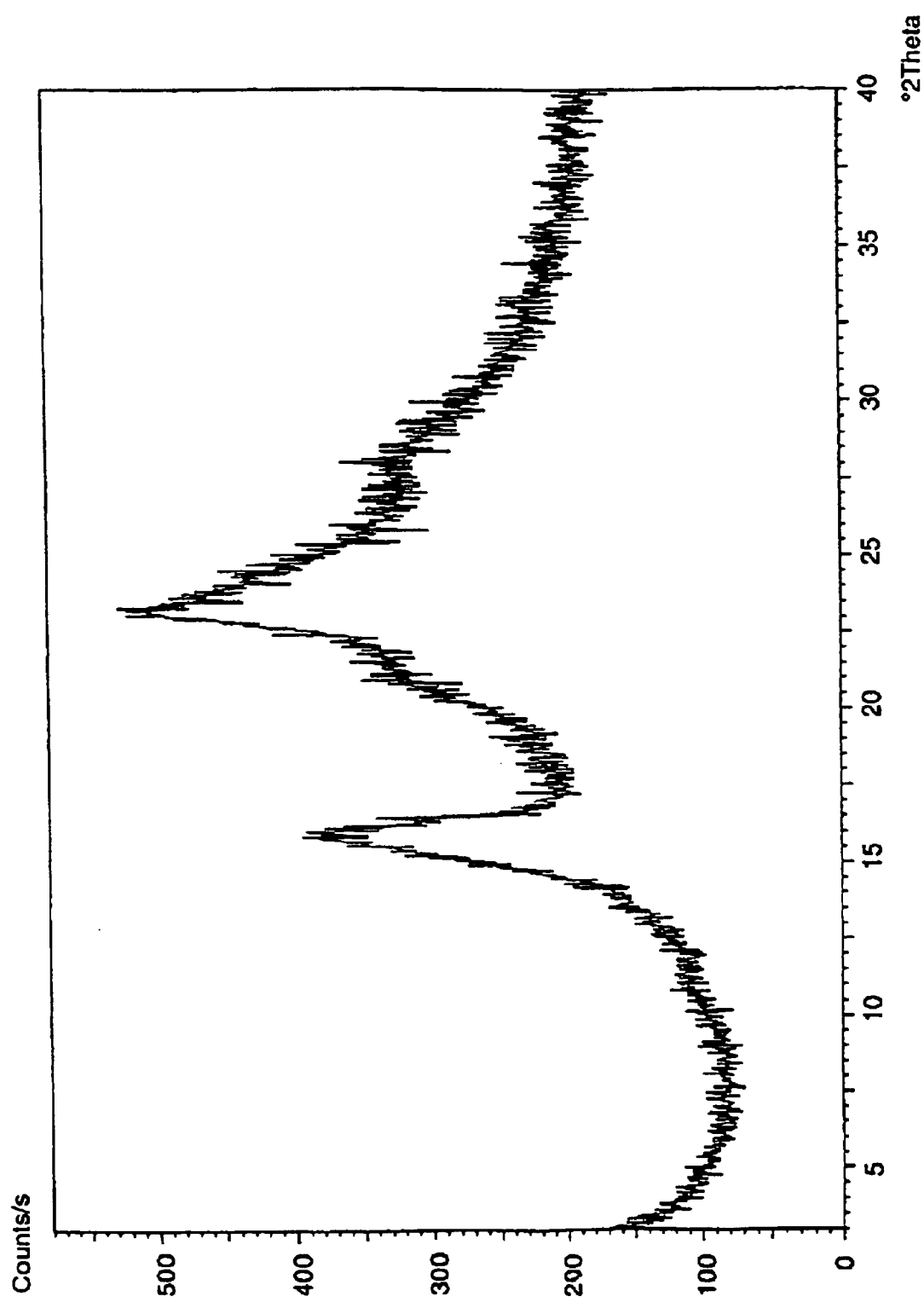
FIG. 26 shows the X-ray powder diffraction pattern of a sample of the amorphous form after 12 months
Figure 27:
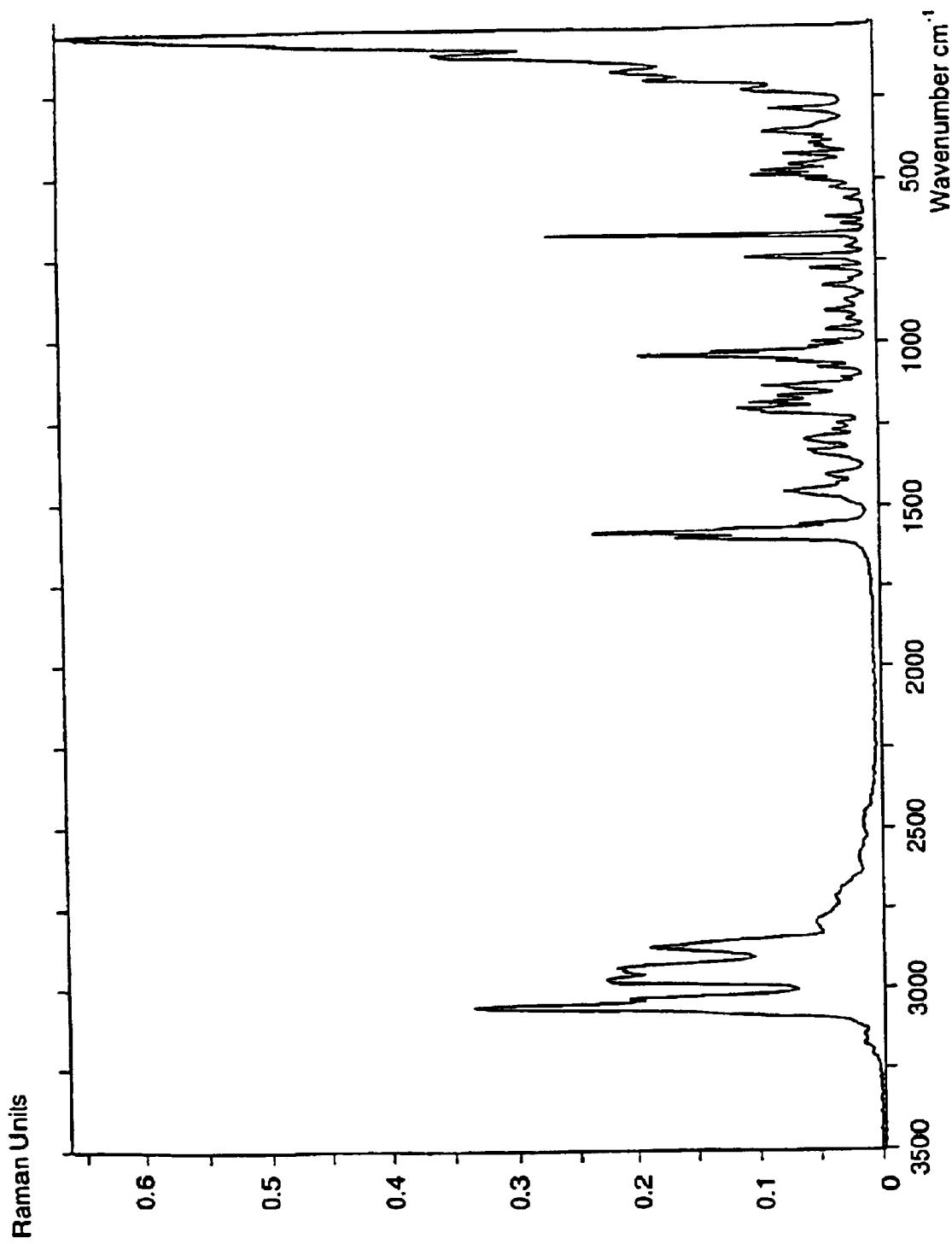
FIG. 27 shows the Raman spectrum of the amorphous form
Figure 28:
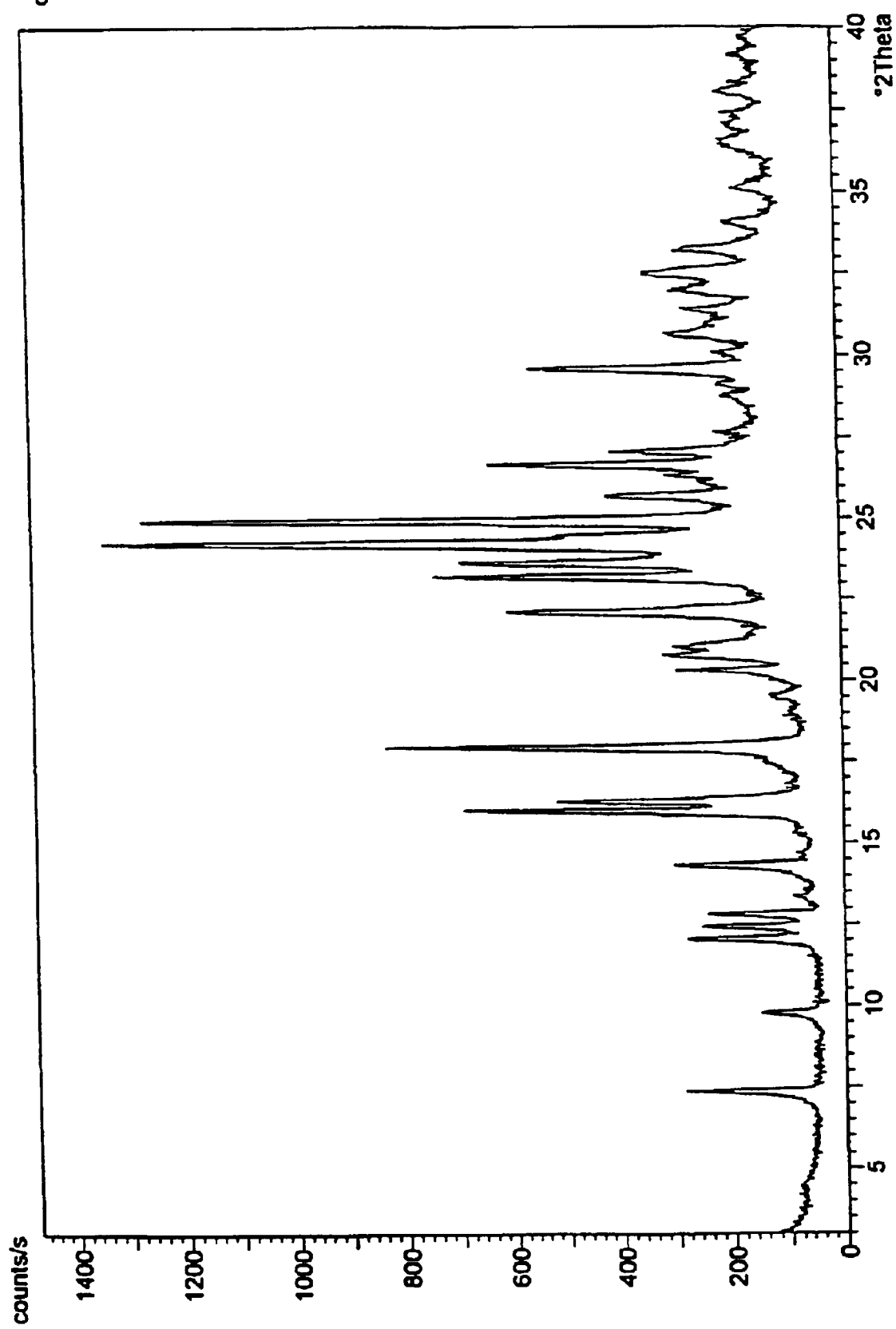
FIG. 28 is a characteristic X-ray powder diffraction pattern of the methanol solvate

What is claimed is:

1. A process for the preparation of polymorphic form II of sertraline hydrochloride, wherein a solution of sertraline free amino is seeded with some crystals, of polymorphic form II before addition of a solution of hydrogen chloride, or wherein a stirred suspension of sertraline hydrochloride polymorphic form V is stirred with some seeding crystals of sertraline hydrochloride polymorphic form II, or wherein sertraline hydrochloride alcohol solvate is dried at temperatures from 0 to 30° C. in a high vacuum of less than 1 mbar, or wherein suspensions of sertraline hydrochloride polymorphic form CSC1, CSC2 or T1 are stirred with some seeding crystals of sertraline hydrochloride polymorphic form II.

2. A process for the preparation of polymorphic form II of sertraline hydrochloride, wherein a solution of sertraline free amine is seeded with some crystals of polymorphic form II and a solution of hydrogen chloride is added.

3. A process according to claim 2, wherein a solution of sertraline free amine in a ketone is used.

4. A process according to claim 2, wherein a solution of sertraline free amine in acetone, methyl ethyl ketone or methyl isobutyl ketone is used.

5. A process according to claim 2, wherein an aqueous solution of hydrogen chloride is used.

6. A process according to claim 2, wherein the seeding crystals of polymorphic form II are added before addition of the solution of hydrogen chloride.

* * * * *